US009150510B2

(12) United States Patent
Ookubo et al.

(10) Patent No.: US 9,150,510 B2
(45) Date of Patent: Oct. 6, 2015

(54) AMINO ACID DERIVATIVE

(75) Inventors: Tomohiro Ookubo, Kato (JP); Ko Nakamura, Kato (JP); Hiroyoshi Nanba, Kato (JP); Hiroyuki Yoshida, Kato (JP); Yoshitaka Nakazawa, Kato (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 721 days.

(21) Appl. No.: 13/119,063

(22) PCT Filed: Sep. 17, 2009

(86) PCT No.: PCT/JP2009/066217
§ 371 (c)(1),
(2), (4) Date: Mar. 15, 2011

(87) PCT Pub. No.: WO2010/032771
PCT Pub. Date: Mar. 25, 2010

(65) Prior Publication Data
US 2011/0172442 A1  Jul. 14, 2011

(30) Foreign Application Priority Data
Sep. 18, 2008 (JP) ................................ 2008-239282

(51) Int. Cl.
| C07D 405/12 | (2006.01) |
| C07D 209/20 | (2006.01) |
| A61K 31/405 | (2006.01) |
| C07C 233/49 | (2006.01) |
| A61K 31/164 | (2006.01) |
| C07C 235/34 | (2006.01) |
| C07C 255/57 | (2006.01) |
| C07C 279/14 | (2006.01) |
| C07C 323/59 | (2006.01) |
| C07D 207/452 | (2006.01) |
| C07D 307/85 | (2006.01) |
| C07D 311/12 | (2006.01) |
| C07D 405/06 | (2006.01) |

(52) U.S. Cl.
CPC ............ *C07D 209/20* (2013.01); *C07C 233/49* (2013.01); *C07C 235/34* (2013.01); *C07C 255/57* (2013.01); *C07C 279/14* (2013.01); *C07C 323/59* (2013.01); *C07D 207/452* (2013.01); *C07D 307/85* (2013.01); *C07D 311/12* (2013.01); *C07D 405/06* (2013.01); *C07D 405/12* (2013.01)

(58) Field of Classification Search
None
See application file for complete search history.

(56) References Cited

U.S. PATENT DOCUMENTS

| 2006/0040334 | A1 | 2/2006 | Thompson |
| 2007/0066646 | A1 | 3/2007 | Clauzel et al. |
| 2008/0262224 | A1 | 10/2008 | Clark et al. |
| 2008/0269282 | A1* | 10/2008 | Clauzel et al. ................ 514/311 |
| 2009/0149658 | A1 | 6/2009 | Nakamura et al. |
| 2010/0008976 | A1 | 1/2010 | Hensel et al. |

FOREIGN PATENT DOCUMENTS

| CN | 101195582 A | 6/2008 |
| EP | 0 288 176 A1 | 5/1988 |
| GB | 2389582 A | 12/2003 |
| JP | A-63-258841 | 10/1988 |
| JP | A-2005-521892 | 7/2005 |
| JP | A-2007-520491 | 7/2007 |
| JP | A-2007-262050 | 10/2007 |
| JP | A-2008-508348 | 3/2008 |
| SU | 1066984 A | 1/1984 |
| WO | WO 2005/061475 A2 | 7/2005 |
| WO | WO 2005/072723 A1 | 8/2005 |
| WO | WO 2006/013209 A2 | 2/2006 |
| WO | WO 2007/030761 A2 | 3/2007 |
| WO | WO 2007/086354 A1 | 8/2007 |
| WO | WO 2008/009655 A2 | 1/2008 |

OTHER PUBLICATIONS

Nomura, et al., Bioorg. Med. Chem. 11:3807 (2003).*
Apr. 26, 2012 Search Report issued in European Patent Application No. 09814615.2.
Katritzky et al., Chiral N-(Coumarin-3-ylcarbonyl)-α-amino Acids: Fluorescent Markers for Amino Acids and Dipeptides, Synthesis, May 16, 2008, pp. 2013-2022, vol. 2008, No. 13, Georg Thieme Verlag Stuttgart, New York.
Office Action issued in Korean Patent Application No. 10-2011-7006312 dated Jun. 28, 2013 (with partial translation).
Weiss, B., "Synthesis of Long Chain Fatty Acid Amides of Amino Acids," Journal of Organic Chemistry, 1959, vol. 24, p. 1367.
Shalaby, A.M., "Acryloyl Amino Acid Conjugates of Anticipated Anti-Allergic Activity," Biomedical Problems, 1999, vol. 58, p. 9-38
Takeuchi, H., "Further Study on Effects of N-β-Phenylpropionyl-L-Tyrosine and Its Derivatives on the Excitability of an Identifiable Giant Neuron of Achatina Fulica Ferussac," Comparative Biochemistry and Physiology, (1983), vol. 75C, p. 329-335.
Murata, M., "Hydroxycinnamic Acid Derivatives and p-Coumaroyl-(L)-tryprophan, A Novel Hydroxycinnamic Acid Derivative, from Coffee Beans," Bioscience, Biotechnology and Biochemistry, (1995), vol. 59(10), p. 1887-1890.
Ihara, Y., "Asymmetric Interaction of Optically Active Polymers with Asymmetric Small Molecules. IV. Effect of Hydrophobic Groups on Asymmetric Interaction," Journal of Polymer Science, Polymer Chemistry Edition, (1972), vol. 10, p. 3569-3576.

(Continued)

*Primary Examiner* — Michael Barker
(74) *Attorney, Agent, or Firm* — Oliff PLC

(57) ABSTRACT

The amino acid derivative of the present invention provides a novel compound that shows excellent analgesic action. The amino acid derivative of the present invention is a novel compound that shows excellent analgesic action to not only a model animal for nociceptive pains but also a model animal for neuropathic pains, so that the amino acid derivative is very useful as a drug for treating various pain diseases.

25 Claims, No Drawings

(56) References Cited

OTHER PUBLICATIONS

International Preliminary Report on Patentability and Written Opinion issued in International Application No. PCT/JP2009/066217, dated Apr. 19, 2011 (with translation).

International Search Report issued in International Application No. PCT/JP2009/066217, dated Dec. 28, 2009 (with translation).

Office Action issued in Russian Patent Application No. 2011114991 issued Jul. 12, 2013 (with translation).

Mar. 26, 2013 Russian Office Action issued in Russian Patent Application No. 2011114991/04(022263).

Camail et al., "Copolymerization of N-acryloyl-L-valine and N-acryloyl-L-phenylalanine with acrylamide," *Macromolecular Chemistry and Physics*, 1995, pp. 167-175, vol. 196, No. 1 (with Abstract).

Oiinisiii et al., "Synthesis of Crotonylamino Acids," *Memoirs of the Faculty of Science, Kyushu University, Series C: Chemistry*, 1962, pp. 27-31, vol. 5, No. 1.

Pavlinec et al., "The Depletion of Substituted Phenolic Stabilizers by Conjugate C-Addition to Acrylic Monomers in Multicomponent Systems," *Macromolecular Materials and Engineering*, 2012, pp. 1005-1013, vol. 297, No. 10.

LV et al., "N-Acryloylaspartic acid," *Acta Crystallographica, Section E: Structure Reports Online*, 2007, pp. o207-o209, vol. E65, No. 1.

Heilmann et al., "Acrylic-Functional Aminocarboxylic Acids and Derivatives as Components of Pressure-Sensitive Adhesives," *Journal of Applied Polymer Science*, 1979, pp. 1551-1564, vol. 24, No. 6.

Jung et al., "Synthesis and Characterization of Stimuli Responsive Block Copolymers Via Atom Transfer Radical Polymerization," *Polymer Preprints*, 2008, pp. 479-480, vol. 49, No. 2.

Wu et al., "N-Acryloylphenylalanine," *Acta Crystallographica, Section E: Structure Reports Online*, 2008, pp. o1483 and Sup-1-7, vol. E64, No. 8.

Iwakura et al., "Synthesis and Polymerization of N-[1(1-Substituted-2-oxopropyl)]acrylamides and -methacrylamides. Copolymerization of These Monomers with Styrene and Substituent Effects," *Journal of Polymer Science, Part A-1: Polymer Chemistry*, 1967, pp. 1599-1607, vol. 5, No. 7.

Iwakura et al., "Synthesis of N-[1-(1-Substituted 2-oxopropyl)]acrylamides and -methacrylamides. Isolation and Some Reactions of Intermediates of the Dakin-West Reaction," *Journal of Organic Chemistry*, 1967, pp. 440-443, vol. 32, No. 2.

\* cited by examiner

AMINO ACID DERIVATIVE

TECHNICAL FIELD

The present invention relates to an amino acid derivative and salt and hydrate thereof that are pharmaceutically acceptable, and a pharmaceutical agent containing the compound as an active ingredient.

BACKGROUND ART

At present, non-steroidal anti-inflammatory drugs (NSAIDs), non-narcotic analgesics, narcotic analgesics, and the like are used against general "pains," so that therapeutic methods therefor have begun to be established. However, there are hardly any analgesics that can satisfy the neuropathic pains under the current situation.

"Pains" are roughly classified by causes of diseases into nociceptive pain (so-called general "pain") caused by a strong stimulus (nociceptive stimulus) that would result in damages to body tissues, and neuropathic pain (neurogenic pain), which is a disease pain resulting from an injury or malfunction of the central or peripheral nerve. This neuropathic pain causes, in addition to a spontaneous pain, a symptom such as a hyperalgesia that lowers the pain thresholds against the nociceptive stimulus and a severe pain (allodynia) caused by tactile stimulation that usually does not induce the pain. Once the morbid state is completed, it turns chronically whereby the outcome is very intractable.

As a result of intensive studies on the compounds that show effects on various pains, the present inventors have found that the amino acid derivative of the present invention has excellent analgesic actions to not only a nociceptive pain model animal but also a neuropathic pain model animal. As amino acid derivatives, N-cinnamoyl-tryptophan as an intermediate of a compound having an anti-allergic action (Non-Patent Publication 1), N-cinnamoyl-L-tryptophan, N-cinnamoyl-D-tryptophan, and N-3-chlorocinnamoyl-tryptophan that suppress excitation of gigantic neural cells of East African land snail (Non-Patent Publication 2), p-coumaroyl-L-tryptophan and caffeoyl-tryptophan, which are isolated substances from coffee beans (Non-Patent Publication 3), N-acrylyl-L-tryptophan and N-acrylyl-L-leucine, which are monomers of a copolymer (Non-Patent Publication 4) are disclosed; however, any one of the publications do not describe at all that these compounds are useful as pharmaceutical agent, and especially as analgesics. In addition, Patent Publication 1 describes p-coumaroyl-L-tryptophan, N-caffeoyl-L-tryptophan, p-coumaroyl-L-tyrosine, or the like that is extracted from a plant; however, the publication does not describe that these have analgesic actions, and the like.

PRIOR ART PUBLICATIONS

Patent Publication(s)

Patent Publication 1: International Publication WO 2008/009655

Non-Patent Publications

Non-Patent Publication 1: *"Biomedical Problems,"* 58, 9-38 (1999)

Non-Patent Publication 2: *"Comparative Biochemistry and Physiology,"* 75, 329-335 (1983)

Non-Patent Publication 3: *"Bioscience, Biotechnology and Biochemistry,"* 59(10), 1887-1890 (1995)

Non-Patent Publication 4: *"Journal of Polymer Science: Polymer Chemistry Edition,"* 10, 3569-3576 (1972)

SUMMARY OF THE INVENTION

Problems to be Solved by the Invention

An object of the present invention is to provide an amino acid derivative which is useful as a pharmaceutical agent such as an analgesic.

Means to Solve the Problems

As a result of intensive studies on compounds showing effects against various pains, the present inventors have found that an amino acid derivative represented by the following structural formula (I') has an excellent analgesic action in a pathological model animal for nociceptive pains and a pathological model animal for neuropathic pains, so that the amino acid derivative is useful as a pharmaceutical agent such as an analgesic. The present invention has been perfected thereby.

Effects of the Invention

The amino acid derivative of the present invention is a novel compound that shows excellent analgesic action to not only a model animal for nociceptive pains but also a model animal for neuropathic pains, so that the amino acid derivative is very useful as a drug for treating various pain diseases.

MODES FOR CARRYING OUT THE INVENTION

The present invention relates to a novel amino acid derivative, and salt and hydrate thereof that are pharmaceutically acceptable, wherein the amino acid derivative is represented by the following general formula (I):

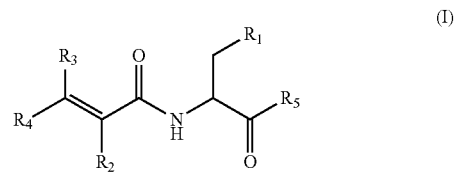

wherein $R_1$ stands for an indole of which N-position may be substituted with formyl, benzyl, or alkyl having 1 to 6 carbon atoms, a phenyl substituted with hydroxy or alkoxy having 1 to 4 carbon atoms, an alkyl having 1 to 6 carbon atoms which may be substituted with carboxy, amino, guanidino, carbamoyl, or alkylsulfanyl having 1 to 4 carbon atoms, or a hydroxy;

$R_2$ stands for a hydrogen, an alkyl having 1 to 4 carbon atoms, or a cyano;

$R_3$ stands for a hydrogen or an alkyl having 1 to 4 carbon atoms;

$R_4$ stands for a hydrogen, an alkyl having 1 to 4 carbon atoms, or a phenyl which may be substituted with one or two substituents selected from hydroxy, halogen, cyano, trifluoromethyl, phenoxy, alkyl having 1 to 6 carbon atoms, and alkoxy having 1 to 4 carbon atoms;

$R_5$ stands for a hydroxy or an amino, or $R_2$ and $R_4$ may be bound to form a benzofuran ring or a coumarin ring, with proviso that in a case where $R_2$ is a hydrogen and $R_4$ is a phenyl substituted with hydroxy or chlorine, a phenyl substituted with hydroxy and methoxy, or an unsubstituted phenyl, $R_1$ stands for a substituent other than an unsubstituted indole and hydroxyphenyl; or in a case where $R_2$ is a hydrogen and $R_4$ is a phenyl substituted with methyl, $R_1$ stands for a substituent other than a phenyl substituted with hydroxy or an alkoxy having 1 to 4 carbon atoms; or in a case where $R_2$ is a hydrogen and $R_4$ is a phenyl substituted with hydroxy, $R_1$ stands for a substituent other than a carboxymethyl; or in a case where $R_2$ and $R_4$ are hydrogen, $R_1$ stands for a substituent other than an unsubstituted alkyl and an unsubstituted indole.

Also, the present invention relates to a pharmaceutical agent such as an analgesic comprising, as an active ingredient, at least one member of an amino acid derivative, and salt and hydrate thereof that are pharmaceutically acceptable, wherein the amino acid derivative is represented by the following general formula (I'):

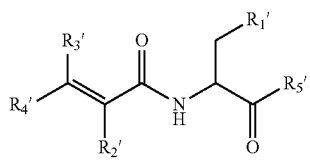

(I')

wherein $R_1'$ stands for an indole of which N-position may be substituted with formyl, benzyl, or alkyl having 1 to 6 carbon atoms, a phenyl substituted with hydroxy or alkoxy having 1 to 4 carbon atoms, an alkyl having 1 to 6 carbon atoms which may be substituted with carboxy, amino, guanidino, carbamoyl, or alkylsulfanyl having 1 to 4 carbon atoms, or a hydroxy;

$R_2'$ stands for a hydrogen, an alkyl having 1 to 4 carbon atoms, or a cyano;

$R_3'$ stands for a hydrogen or an alkyl having 1 to 4 carbon atoms;

$R_4'$ stands for a hydrogen, an alkyl having 1 to 4 carbon atoms, or a phenyl which may be substituted with one or two substituents selected from hydroxy, halogen, cyano, trifluoromethyl, phenoxy, alkyl having 1 to 6 carbon atoms, and alkoxy having 1 to 4 carbon atoms;

$R_5'$ stands for a hydroxy or an amino, or $R_2'$ and $R_4'$ may be bound to form a benzofuran ring or a coumarin ring.

The general formulas in a case where $R_2$ and $R_4$ are bound to form a benzofuran ring or a coumarin ring are each of formulas given below. The same applies to a case of $R_2'$ and $R_4'$.

In the substituents of the general formulas (I) and (I') mentioned above, the alkyl having 1 to 4 carbon atoms stands for a linear or branched alkyl group, and the alkyl group is preferably, a methyl, an ethyl, a propyl, an isopropyl, a butyl, an isobutyl, a sec-butyl, a t-butyl, or the like. The alkyl having 1 to 6 carbon atoms stands for a linear or branched alkyl group, and the alkyl group is preferably, a methyl, an ethyl, a propyl, an isopropyl, a butyl, an isobutyl, a sec-butyl, a t-butyl, a pentyl, an isopentyl, a neopentyl, a t-pentyl, a hexyl, an isohexyl or the like. The alkoxy having 1 to 4 carbon atoms stands for a linear or branched alkoxy group, and the alkoxy group is preferably a methoxy, an ethoxy, a propyloxy, an isopropyloxy, a butyloxy, or the like. The halogen stands for a fluorine, a chlorine, a bromine, an iodine, or the like.

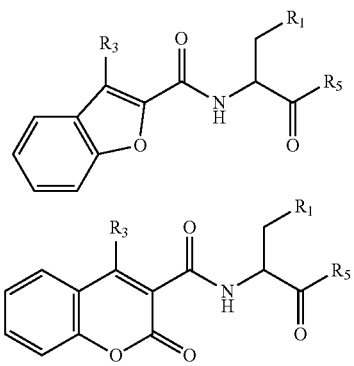

Among the compounds of the present invention, preferred compounds are as follows.

$N^\alpha$-Acryloyl-L-tryptophan [Compound 1]
$N^\alpha$-[3-(2-Hydroxyphenyl)acryloyl]-L-tryptophan [Compound 2]
$N^\alpha$-[3-(2-Fluorophenyl)acryloyl]-L-tryptophan [Compound 3]
$N^\alpha$-[3-(3-Fluorophenyl)acryloyl]-L-tryptophan [Compound 4]
$N^\alpha$-[3-(4-Fluorophenyl)acryloyl]-L-tryptophan [Compound 5]
$N^\alpha$-[3-(3-Hydroxyphenyl)acryloyl]-L-tryptophan [Compound 6]
$N^\alpha$-[3-(4-Hydroxyphenyl)acryloyl]-L-tryptophan [Compound 7]
$N^\alpha$-(3-Phenylacryloyl)-L-tryptophan [Compound 8]
$N^\alpha$-[3-(2-Cyanophenyl)acryloyl]-L-tryptophan [Compound 9]
$N^\alpha$-[3-(2-Trifluoromethylphenyl)acryloyl]-L-tryptophan [Compound 10]
$N^\alpha$-[3-(2-Methoxyphenyl)acryloyl]-L-tryptophan [Compound 11]
$N^\alpha$-[3-(2-Chlorophenyl)acryloyl]-L-tryptophan [Compound 12]
$N^\alpha$-[3-(2,6-Difluorophenyl)acryloyl]-L-tryptophan [Compound 13]
$N^\alpha$-[3-(2,4-Difluorophenyl)acryloyl]-L-tryptophan [Compound 14]
$N^\alpha$-[3-(2,5-Difluorophenyl)acryloyl]-L-tryptophan [Compound 15]
$N^\alpha$-{3-[3,5-Bis(trifluoromethyl)phenyl]acryloyl}-L-tryptophan [Compound 16]
$N^\alpha$-[3-(3-Cyanophenyl)acryloyl]-L-tryptophan [Compound 17]
$N^\alpha$-[3-(4-Phenoxyphenyl)acryloyl]-L-tryptophan [Compound 18]
$N^\alpha$-[3-(4-Cyanophenyl)acryloyl]-L-tryptophan [Compound 19]
$N^\alpha$-(Benzofuran-2-carbonyl)-L-tryptophan [Compound 20]
$N^\alpha$-(Coumarin-3-carbonyl)-L-tryptophan [Compound 21]
$N^\alpha$-[2-Cyano-3-(2-fluorophenyl)acryloyl]-L-tryptophan [Compound 22]
$N^\alpha$-[3-(2-Fluorophenyl)acryloyl]-L-tryptophanamide [Compound 23]
$N^\alpha$-[3-(2-Fluorophenyl)acryloyl]-D-tryptophan [Compound 24]
$N^\alpha$-(2-Cyano-3-phenylacryloyl)-L-tryptophan [Compound 25]
$N^\alpha$-[3-(2-Hydroxyphenyl)acryloyl]-1-methyl-L-tryptophan [Compound 26]

N<sup>α</sup>-[3-(2-Fluorophenyl)acryloyl]-1-methyl-L-tryptophan [Compound 27]
N<sup>α</sup>-[3-(4-Fluorophenyl)acryloyl]-1-methyl-L-tryptophan [Compound 28]
1-Methyl-N<sup>α</sup>-(3-phenylacryloyl)-L-tryptophan [Compound 29]
N<sup>α</sup>-[3-(2-Cyanophenyl)acryloyl]-1-methyl-L-tryptophan [Compound 30]
N<sup>α</sup>-[3-(2,6-Difluorophenyl)acryloyl]-1-methyl-L-tryptophan [Compound 31]
N<sup>α</sup>-[3-(2,4-Difluorophenyl)acryloyl]-1-methyl-L-tryptophan [Compound 32]
N<sup>α</sup>-[3-(2,5-Difluorophenyl)acryloyl]-1-methyl-L-tryptophan [Compound 33]
N<sup>α</sup>-[3-(3-Cyanophenyl)acryloyl]-1-methyl-L-tryptophan [Compound 34]
1-Methyl-N<sup>α</sup>-[3-(4-phenoxyphenyl)acryloyl]-L-tryptophan [Compound 35]
N<sup>α</sup>-[3-(4-Cyanophenyl)acryloyl]-1-methyl-L-tryptophan [Compound 36]
N<sup>α</sup>-[2-Cyano-3-(2-fluorophenyl)acryloyl]-1-methyl-L-tryptophan [Compound 37]
N-Acryloyl-O<sup>4</sup>-methyl-L-tyrosine [Compound 38]
N-[3-(2-Hydroxyphenyl)acryloyl]-O<sup>4</sup>-methyl-L-tyrosine [Compound 39]
N-[3-(2-Fluorophenyl)acryloyl]-O<sup>4</sup>-methyl-L-tyrosine [Compound 40]
N-[3-(3-Fluorophenyl)acryloyl]-O<sup>4</sup>-methyl-L-tyrosine [Compound 41]
N-[3-(4-Fluorophenyl)acryloyl]-O<sup>4</sup>-methyl-L-tyrosine [Compound 42]
N-[3-(3-Hydroxyphenyl)acryloyl]-O<sup>4</sup>-methyl-L-tyrosine [Compound 43]
N-[3-(4-Hydroxyphenyl)acryloyl]-O<sup>4</sup>-methyl-L-tyrosine [Compound 44]
O<sup>4</sup>-Methyl-N-(3-phenylacryloyl)-L-tyrosine [Compound 45]
N-[3-(2-Cyanophenyl)acryloyl]-O<sup>4</sup>-methyl-L-tyrosine [Compound 46]
O<sup>4</sup>-Methyl-N-P-(2-trifluoromethylphenyl)acryloyl]-L-tyrosine [Compound 47]
N-[3-(2-Methoxyphenyl)acryloyl]-O<sup>4</sup>-methyl-L-tyrosine [Compound 48]
N-[3-(2-Chlorophenyl)acryloyl]-O<sup>4</sup>-methyl-L-tyrosine [Compound 49]
N-[3-(2,6-Difluorophenyl)acryloyl]-O<sup>4</sup>-methyl-L-tyrosine [Compound 50]
N-[b 3-(2,4-Difluorophenyl)acryloyl]-O<sup>4</sup>-methyl-L-tyrosine [Compound 51]
N-[3-(2,5-Difluorophenyl)acryloyl]-O<sup>4</sup>-methyl-L-tyrosine [Compound 52]
N-{3-[3,5-Bis(trifluoromethyl)phenyl]acryloyl}-O<sup>4</sup>-methyl-L-tyrosine [Compound 53]
N-[3-(3-Cyanophenyl)acryloyl]-O<sup>4</sup>-methyl-L-tyrosine [Compound 54]
O<sup>4</sup>-Methyl-N-[3-(4-phenoxyphenylacryloyl)]-L-tyrosine [Compound 55]
N-[3-(4-Cyanophenyl)acryloyl]-O<sup>4</sup>-methyl-L-tyrosine [Compound 56]
N-(Benzofuran-2-carbonyl)-O<sup>4</sup>-methyl-L-tyrosine [Compound 57]
N-(Coumarin-3-carbonyl)-O<sup>4</sup>-methyl-L-tyrosine [Compound 58]
N-[3-(2-Fluorophenyl)acryloyl]-L-leucine [Compound 59]
N-[3-(2-Fluorophenyl)acryloyl]-L-glutamic acid [Compound 60]
N<sup>α</sup>-[3-(2-Fluorophenyl)acryloyl]-L-lysine hydrochloride [Compound 61]
N-[3-(2-Fluorophenyl)acryloyl]-L-tyrosine [Compound 62]
N<sup>α</sup>-[3-(2-Fluorophenyl)acryloyl]-L-ornithine hydrochloride [Compound 63]
N<sup>α</sup>-[3-(2-Fluorophenyl)acryloyl]-L-arginine [Compound 64]
N<sup>α</sup>-[3-(2-Fluorophenyl)acryloyl]-L-glutamine [Compound 65]
N-[3-(2-Fluorophenyl)acryloyl]-L-serine [Compound 66]
N-[3-(2-Fluorophenyl)acryloyl]-L-methionine [Compound 67]
N<sup>α</sup>-[3-(2-Fluorophenyl)acryloyl]-1-formyl-L-tryptophan [Compound 68]
1-Ethyl-N<sup>α</sup>-[3-(2-fluorophenyl)acryloyl]-L-tryptophan [Compound 69]
N<sup>α</sup>-[3-(2-Fluorophenyl)acryloyl]-1-i-propyl-L-tryptophan [Compound 70]
1-n-Butyl-N<sup>α</sup>-[3-(2-fluorophenyl)acryloyl]-L-tryptophan [Compound 71]
1-Benzyl-N<sup>α</sup>-[3-(2-fluorophenyl)acryloyl]-L-tryptophan [Compound 72]
N<sup>α</sup>-[3-(2-Methylphenyl)acryloyl]-L-tryptophan [Compound 73]
N<sup>α</sup>-[3-(3-Methylphenyl)acryloyl]-L-tryptophan [Compound 74]
N<sup>α</sup>-[3-(4-Methylphenyl)acryloyl]-L-tryptophan [Compound 75]
N<sup>α</sup>-[3-(4-n-Butylphenyl)acryloyl]-L-tryptophan [Compound 76]
N<sup>α</sup>-[3-(4-i-Propylphenyl)acryloyl]-L-tryptophan [Compound 77]
N<sup>α</sup>-Crotonoyl-L-tryptophan [Compound 78]
N<sup>α</sup>-3-Methylcrotonoyl-L-tryptophan [Compound 79]
N<sup>α</sup>-Tigloyl-L-tryptophan [Compound 80]
N<sup>α</sup>-trans-2-Hexenoyl-L-tryptophan [Compound 81]
N<sup>α</sup>-(2-Methyl-3-phenylacryloyl)-L-tryptophan [Compound 82]

Among the above compounds 1 to 82, the compounds 1, 2, 4 to 11, 13, 14 and 38 were synthesized as sodium salts, and the compound 60 was synthesized as a disodium salt, in the Examples described below.

A general method for producing the compound of the present invention will be given hereinbelow. The compound of the present invention represented by the above-mentioned general formula (I) can be produced according to the method (1) or (2) described below (the same applies to the compound of the present invention represented by the general formula (I')). Here, an example of a method for producing an amino acid derivative in L-form, which is a compound of the present invention, will be given hereinbelow, and a D-form, a stereoisomer thereof, can be also synthesized by a similar route.

(1) In a case where $R_1$ is an indole of which N position may be substituted with formyl, alkyl or benzyl, an alkoxyphenyl, a hydroxy, or an alkyl which may be substituted with carboxy, amino, guanidino or alkylsulfanyl;

$R_2$ is a hydrogen or an alkyl;

$R_3$ is a hydrogen or an alkyl;

$R_4$ is hydrogen, an alkyl, or a phenyl which may be substituted with one or two substituents selected from hydroxy, halogen, cyano, trifluoromethyl, phenoxy, alkyl and alkoxy; and $R_5$ is a hydroxy, or $R_2$ and $R_4$ are bound to form a benzofuran ring or a coumarin ring, the synthesis was carried out by a route shown in the following scheme:

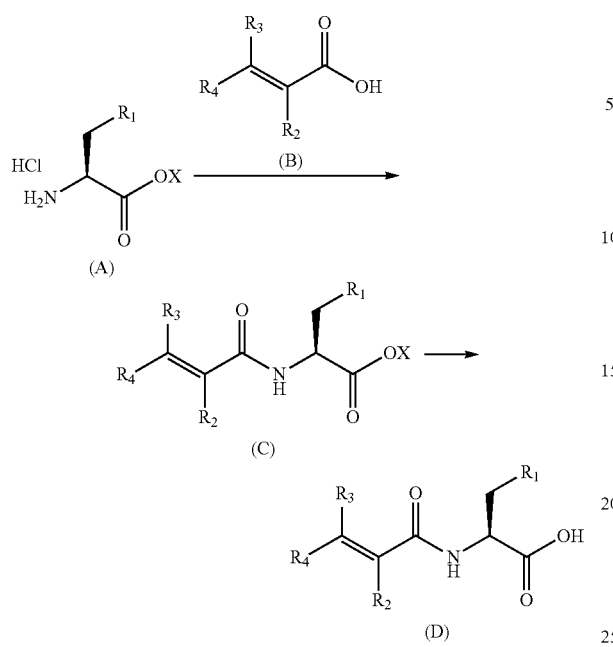

(A) (B) (C) (D)

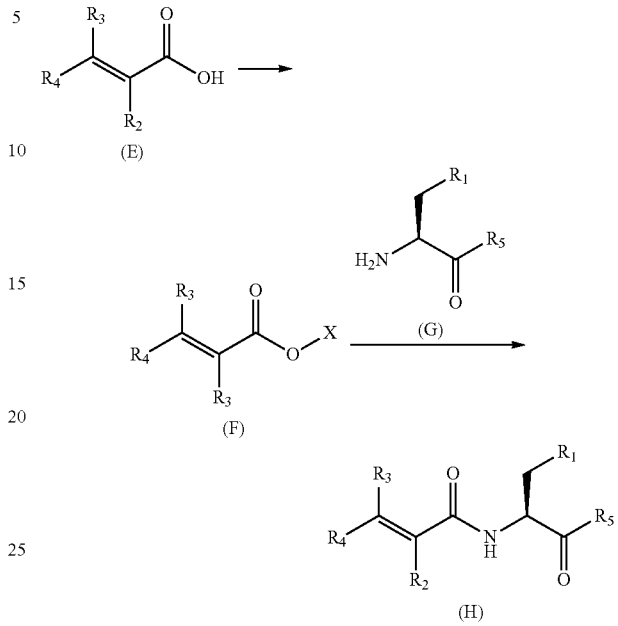

(E) (F) (G) (H)

A compound of the general formula (C) can be obtained by reacting a compound of the general formula (A) and a compound of the general formula (B) in a solvent which is inert to the reaction, in the presence of an organic base such as triethylamine, N,N-diisopropylethylamine, or morpholine, using a suitable condensing agent, at room temperature for usually 1 to 24 hours. The inert solvent includes, for example, halogenated hydrocarbon-based solvents, such as dichloromethane, 1,2-dichloroethane and chloroform; ether-based solvents, such as tetrahydrofuran (THF), 1,4-dioxane, 1,2-dimethoxyethane and diethyl ether; aromatic hydrocarbon-based solvents, such as benzene, toluene and xylene; and the like. Also, dimethylformamide (DMF) or dimethylsulfoxide (DMSO) may be used. The condensing agent includes water-soluble carbodiimide hydrochloride (WSC.HCl), dicyclohexylcarbodiimide (DCC), DCC-HOBt, carbonyldiimidazole (CDI), and the like.

A compound of the general formula (D) can be obtained by subjecting a compound of the general formula (C) to an alkaline hydrolysis reaction with an aqueous solution of an inorganic base such as sodium hydroxide, potassium hydroxide or calcium hydroxide, in an alcohol-based solvent such as methanol, ethanol or 2-propanol. In addition, when a protecting group is present on $R_1$, a compound of the general formula (D) can be obtained by carrying out deprotection under appropriate conditions. For example, the deprotection can be achieved by a treatment with an inorganic acid in a case where a protecting group is t-butoxycarbonyl, or with an organic acid in a case where a protecting group is a 2,2,4,6,7-pentamethyldihydrobenzofuran-5-sulfonyl group. Here, the inorganic acid includes hydrogen chloride-dioxane, hydrogen chloride-ethyl acetate, and the like; and the organic acid includes trifluoroacetic acid, and the like.

(2) In a case where $R_1$ is an indole which may be substituted with formyl, alkyl or benzyl, a phenyl substituted with hydroxyl or alkoxy, or a carbamoylalkyl, $R_2$ is a hydrogen, $R_3$ is a hydrogen or a cyano, $R_4$ is a phenyl which may be substituted with one or two substituents selected from halogen and cyano, and $R_5$ is a hydroxyl or an amino, the synthesis was carried out by a route shown in the following scheme:

A compound of the general formula (F), which is an active ester form, can be obtained by reacting the compound of the general formula (E) in a solvent which is inert to the reaction, in the presence of a suitable condensing agent, using a suitable activating reagent, at room temperature for usually 1 hour to 24 hours. The compound of the general formula (H) can be obtained by reacting the compound of the general formula (F) and the compound of the general formula (G) in the presence of an inorganic base such as sodium hydrogencarbonate, potassium hydrogencarbonate, sodium carbonate or potassium carbonate, in a solvent which is inert to the reaction, at room temperature for usually 1 hour to 30 hours. Here, the inert solvent includes, for example, halogenated hydrocarbon-based solvents, such as dichloromethane, 1,2-dichloroethane and chloroform; ether-based solvents, such as THF, 1,4-dioxane, 1,2-dimethoxyethane and diethyl ether; aromatic hydrocarbon-based solvents, such as benzene, toluene and xylene; and the like. Also, a mixed solvent such as 1,4-dioxane-water or THF-DMF may be used. In addition, the condensing agent includes WSC.HCl, DCC, DCC-HOBt, CDI, and the like; and the activating reagent includes N-hydroxysuccinic acid imide, phenol, p-nitrophenol, and the like.

The compounds represented by the general formula (I) and (I') mentioned above includes, in a case where a pharmaceutically acceptable salt thereof is present, various kinds of salts thereof. The salts include, for example, addition salts with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid; metal salts of alkali metals such as sodium and potassium, alkaline earth metals such as calcium and magnesium, and aluminum; or salts with bases such as ammonia and organic amines. These salts can be produced from each compound in a free form, or converted reversibly, in accordance with a known method. In addition, in a case where the compounds are present in the state of a stereoisomer such as a cis-trans isomer, an optical isomer or a coordination isomer, or a solvate including a hydrate or a metal complex compound, the present invention embraces any of stereoisomers, solvates, and complex compounds.

The compound of the present invention can be combined with a suitable pharmaceutical carrier or diluent to form a pharmaceutical agent. Also, the compound can be produced into preparations by any ordinary methods, and the compounds can be produced into formulations as an orally administered agent such as a tablet, a capsule, a fine powder, or a liquid, or as a parenterally administered agent for subcutaneous administration, intramuscular administration, intrarectal administration, or intranasal administration. In the formulation, the compound of the present invention may be used in the form of a pharmaceutically acceptable salt thereof, and the compounds can be used alone or in a proper combination. Further, it may be made into a combination drug with another pharmaceutically active ingredient.

The desired dose for the compound of the present invention may vary depending upon the subject to be administered, the dose form, the administration method, the administration period, and the like. In order to obtain a desired effect, the compound of the present invention can be generally orally administered in an amount of from 0.5 to 1000 mg for adult, at once or in several divided administrations per day. In the case of the parenteral administration (for example, an injection), the daily dose is preferably from one-tenth to one-third the dose level for each of the doses mentioned above.

EXAMPLES

A melting point was determined using Yamato Scientific, Model MP-21, a melting point measuring instrument. No compensation of the thermometer was made. Nuclear magnetic resonance spectrum ($^1$H-NMR) was measured with a nuclear magnetic resonance analyzer Model ARX500 (Bruker) using TMS ($\delta$=0) as an internal standard substance. Silica gel column chromatography was performed using silica gel BW-127ZH for normal phase chromatography or basic silica gel DM1020 for aminopropyl group-bound chromatography (either, FUJI SILYSIA CHEMICAL LTD.). Thin-layer chromatography was performed using Silica gel F254 (Merck, No. 5715), and detection was made using a UV lamp and a 5% phosphomolybdic acid-ethanol color development reagent. Commercial products themselves were used as the reagents and solvents.

Example 1

Production of Methyl $N^\alpha$-Acryloyl-L-Tryptophanate

Triethylamine (14 mL) was added to a chloroform (120 mL) solution of methyl L-tryptophanate hydrochloride (5.0 g) under ice-cooling, and further acrylic acid (1.6 mL) was added thereto. Next, a methylene chloride (30 mL) solution of DCC (4.9 g) was added dropwise to the mixture. The mixture was stirred at room temperature for 24 hours, and thereafter a half the volume of the solvent was distilled off under a reduced pressure, acetone was added to the residual mixture, and the mixture was allowed to stand in a freezer overnight. Triethylamine hydrochloride and DC urea were filtered off, the solvents of the filtrate was distilled off under a reduced pressure, and the residual oily product obtained was purified by silica gel column chromatography (BW-127ZH, chloroform:methanol=19:1), to give the captioned compound (1.5 g, 28%) as an oily product.

Example 2

Production of Methyl $N^\alpha$-[3-(2-Acetoxyphenyl)acryloyl]-L-Tryptophanate

Triethylamine (4.8 mL), 2-acetoxycinnamic acid (7.1 g) and WSC.HCl (6.6 g) were added to a methylene chloride (180 mL) suspension of methyl L-tryptophanate hydrochloride (7.3 g) at 0° C. The mixture was stirred for 20 hours at room temperature. The reaction mixture was washed with water, and thereafter the organic layer was dried over anhydrous sodium sulfate. The residual oily product obtained by distilling off the solvent under a reduced pressure was purified by silica gel column chromatography (BW-127ZH, chloroform:methanol=100:1), to give the captioned compound (8.9 g, 76%) as crystals.

Example 3

Production of Methyl $N^\alpha$-[3-(3-Acetoxyphenyl)acryloyl]-L-Tryptophanate

The same procedures as in Example 2 were carried out from methyl L-tryptophanate hydrochloride (3.0 g), triethylamine (2.0 mL), 3-acetoxycinnamic acid (2.9 g), WSC.HCl (2.7 g), and methylene chloride (80 mL), to give the captioned compound (4.7 g, 98%) as an amorphous solid.

Example 4

Production of Methyl $N^\alpha$-[3-(4-Acetoxyphenyl)acryloyl]-L-Tryptophanate

The same procedures as in Example 2 were carried out from methyl L-tryptophanate hydrochloride (3.0 g), triethylamine (2.0 mL), 4-acetoxycinnamic acid (2.9 g), WSC.HCl (2.7 g), and methylene chloride (80 mL), to give the captioned compound (4.5 g, 93%) as an oily product.

Example 5

Production of Methyl $N^\alpha$-[3-(2-Fluorophenyl)acryloyl]-L-Tryptophanate

The same procedures as in Example 2 were carried out from methyl L-tryptophanate hydrochloride (5.0 g), triethylamine (2.9 mL), 2-fluorocinnamic acid (3.4 g), WSC.HCl (3.9 g), and methylene chloride (130 mL), to give the captioned compound (7.1 g, 99%) as an oily product.

Example 6

Production of Methyl $N^\alpha$-[3-(3-Fluorophenyl)acryloyl]-L-Tryptophanate

The same procedures as in Example 2 were carried out from methyl L-tryptophanate hydrochloride (4.0 g), triethylamine (2.3 mL), 3-fluorocinnamic acid (2.7 g), WSC.HCl (3.2 g), and methylene chloride (100 mL), to give the captioned compound (4.2 g, 74%) as an oily product.

Example 7

Production of Methyl N$^\alpha$-[3-(4-Fluorophenyl)acryloyl]-L-Tryptophanate

The same procedures as in Example 2 were carried out from methyl L-tryptophanate hydrochloride (4.0 g), triethylamine (4.8 mL), 4-fluorocinnamic acid (2.9 g), WSC.HCl (3.3 g), and methylene chloride (150 mL), to give the captioned compound (4.3 g, 74%) as an oily product.

Example 8

Production of Methyl N$^\alpha$-(3-Phenylacryloyl)-L-Tryptophanate

The same procedures as in Example 2 were carried out from methyl L-tryptophanate hydrochloride (4.0 g), triethylamine (4.8 mL), cinnamic acid (2.6 g), WSC.HCl (3.3 g), and methylene chloride (150 mL), to give the captioned compound (3.7 g, 67%) as an oily product.

Example 9

Production of Methyl N$^\alpha$-[3-2-Cyanophenyl)acryloyl]-L-Tryptophanate

The same procedures as in Example 2 were carried out from methyl L-tryptophanate hydrochloride (4.0 g), triethylamine (2.6 mL), 2-cyanocinnamic acid (3.3 g), WSC.HCl (3.6 g), and methylene chloride (100 mL), to give the captioned compound (5.8 g, 99%) as an oily product.

Example 10

Production of Methyl N$^\alpha$-[3-(2-Trifluoromethylphenyl)acryloyl]-L-Tryptophanate The same procedures as in Example 2 were carried out from methyl L-tryptophanate hydrochloride (3.0 g), triethylamine (2.0 mL), 2-trifluorocinnamic acid (3.1 g), WSC.HCl (2.7 g), and methylene chloride (80 mL), to give the captioned compound (3.4 g, 70%) as an oily product.

Example 11

Production of Methyl N$^\alpha$-[3-(2-Methoxyphenyl)acryloyl]-L-Tryptophanate

The same procedures as in Example 2 were carried out from methyl L-tryptophanate hydrochloride (4.0 g), triethylamine (4.8 mL), 2-methoxycinnamic acid (3.1 g), WSC.HCl (3.3 g), and methylene chloride (150 mL), to give the captioned compound (5.2 g, 88%) as an oily product.

Example 12

Production of Methyl N$^\alpha$-[3-(2-Chlorophenyl)acryloyl]-L-Tryptophanate

The same procedures as in Example 2 were carried out from methyl L-tryptophanate hydrochloride (3.0 g), triethylamine (2.0 mL), 2-chlorocinnamic acid (2.6 g), WSC.HCl (2.7 g), and methylene chloride (80 mL), to give the captioned compound (4.5 g, 99%) as an oily product.

Example 13

Production of Methyl N$^\alpha$-[3-(2,6-Difluorophenyl)acryloyl]-L-Tryptophanate The same procedures as in Example 2 were carried out from methyl L-tryptophanate hydrochloride (3.0 g), triethylamine (2.0 mL), 2,6-difluorocinnamic acid (2.6 g), WSC.HCl (2.7 g), and methylene chloride (80 mL), to give the captioned compound (3.9 g, 85%) as an oily product.

Example 14

Production of Methyl N$^\alpha$-[3-(2,4-Difluorophenyl)acryloyl]-L-Tryptophanate The same procedures as in Example 2 were carried out from methyl L-tryptophanate hydrochloride (3.0 g), triethylamine (2.0 mL), 2,4-difluorocinnamic acid (2.6 g), WSC.HCl (2.7 g), and methylene chloride (80 mL), to give the captioned compound (4.5 g, 99%) as an oily product.

Example 15

Production of Methyl N$^\alpha$-[3-(2,5-Difluorophenyl)acryloyl]-L-Tryptophanate The same procedures as in Example 2 were carried out from methyl L-tryptophanate hydrochloride (3.0 g), triethylamine (2.0 mL), 2,5-difluorocinnamic acid (2.6 g), WSC.HCl (2.7 g), and methylene chloride (80 mL), to give the captioned compound (4.1 g, 90%) as an oily product.

Example 16

Production of Methyl N$^\alpha$-{3-[3,5-Bis(trifluoromethyl)phenyl]acryloyl}-L-Tryptophanate The same procedures as in Example 2 were carried out from methyl L-tryptophanate hydrochloride (3.0 g), triethylamine (2.0 mL), 3,5-bis(trifluoromethyl)cinnamic acid (4.0 g), WSC.HCl (2.7 g), and methylene chloride (80 mL), to give the captioned compound (2.6 g, 64%) as crystals.

Example 17

Production of Methyl N$^\alpha$-[3-(4-Phenoxyphenyl)acryloyl]-L-Tryptophanate

The same procedures as in Example 2 were carried out from methyl L-tryptophanate hydrochloride (3.0 g), triethylamine (2.0 mL), 4-phenoxycinnamic acid (3.4 g), WSC.HCl (2.7 g, 14.1 mmol), and methylene chloride (80 mL), to give the captioned compound (4.9 g, 94%) as an oily product.

Example 18

Production of Methyl N$^\alpha$-(Benzofuran-2-Carbonyl)-L-Tryptophanate

The same procedures as in Example 2 were carried out from methyl L-tryptophanate hydrochloride (4.0 g), triethylamine (2.2 mL), benzofuran-2-carboxylic acid (3.1 g), WSC.HCl (3.6 g), and methylene chloride (100 mL), to give the captioned compound (5.6 g, 98%) as an oily product.

Example 19

Production of Methyl $N^\alpha$-(Coumarin-3-Carbonyl)-L-Tryptophanate

The same procedures as in Example 2 were carried out from methyl L-tryptophanate hydrochloride (3.0 g), triethylamine (2.0 mL), coumarin-3-carboxylic acid (2.7 g), WSC.HCl (2.7 g), and methylene chloride (80 mL), to give the captioned compound (2.0 g, 43%) as an oily product.

Example 20

Production of Methyl 1-Methyl-L-Tryptophanate Hydrochloride

Thionyl chloride (16.7 mL) was added dropwise to methanol (150 mL) at 0° C., and thereafter 1-methyl-L-tryptophanate (10.0 g) was added at room temperature. The mixture was allowed to stir for 20 hours, and thereafter heated and refluxed for 6 hours. To the residue obtained by distilling off the solvent under a reduced pressure was added diethylether, and crystals precipitated were filtered, to give the captioned compound (10.7 g, 87%).

Example 21

Production of Methyl $N^\alpha$-[3-(2-Acetoxyphenyl)acryloyl]-1-Methyl-L-Tryptophanate The same procedures as in Example 2 were carried out from the compound obtained in Example 20 (3.0 g), triethylamine (1.7 mL), 2-acetoxycinnamic acid (2.5 g), WSC.HCl (2.4 g), and methylene chloride (80 mL), to give the captioned compound (3.9 g, 83%) as an oily product.

Example 22

Production of Methyl $N^\alpha$-[3-(2-Fluorophenyl)acryloyl]-1-Methyl-L-Tryptophanate The same procedures as in Example 2 were carried out from the compound obtained in Example 20 (4.0 g), triethylamine (2.3 mL), 2-fluorocinnamic acid (2.7 g), WSC.HCl (3.1 g), and methylene chloride (100 mL), to give the captioned compound (3.1 g, 54%) as an oily product.

Example 23

Production of Methyl $N^\alpha$-[3-(4-Fluorophenyl)acryloyl]-1-Methyl-L-Tryptophanate The same procedures as in Example 2 were carried out from the compound obtained in Example 20 (2.0 g), triethylamine (1.1 mL), 4-fluorocinnamic acid (1.4 g), WSC.HCl (1.6 g), and methylene chloride (80 mL), to give the captioned compound (2.7 g, 94%) as an oily product.

Example 24

Production of Methyl $N^\alpha$-[3-(2,6-Difluorophenyl)acryloyl]-1-Methyl-L-Tryptophanate The same procedures as in Example 2 were carried out from the compound obtained in Example 20 (1.4 g), triethylamine (0,72 mL), 2,6-difluorocinnamic acid (1.0 g), WSC.HCl (1.0 g), and methylene chloride (50 mL), to give the captioned compound (1.1 g, 51%) as an oily product.

Example 25

Production of Methyl $N^\alpha$-[3-(2,4-Difluorophenyl)acryloyl]-1-Methyl-L-Tryptophanate The same procedures as in Example 2 were carried out from the compound obtained in Example 20 (1.0 g), triethylamine (0.54 mL), 2,4-difluorocinnamic acid (0.72 g), WSC.HCl (0.75 g), and methylene chloride (40 mL), to give the captioned compound (0.73 g, 49%) as an oily product.

Example 26

Production of Methyl $N^\alpha$-[3-(2,5-Difluorophenyl)acryloyl]-1-Methyl-L-Tryptophanate The same procedures as in Example 2 were carried out from the compound obtained in Example 20 (2.0 g), triethylamine (1.1 mL), 2,5-difluorocinnamic acid (1.5 g), WSC.HCl (1.6 g), and methylene chloride (80 mL), to give the captioned compound (2.9 g, 98%) as an oily product.

Example 27

Production of Methyl 1-Methyl-$N^\alpha$-[3-(4-Phenoxyphenyl)acryloyl]-L-Tryptophanate The same procedures as in Example 2 were carried out from the compound obtained in Example 20 (1.0 g), triethylamine (0.54 mL), 4-phenoxycinnamic acid (0.94 g), WSC.HCl (0.75 g), and methylene chloride (40 mL), to give the captioned compound (0.93 g, 55%) as an oily product.

Example 28

Production of Methyl $N^\alpha$-tert-Butoxycarbonyl-1-Formyl-L-Tryptophanate

To DMF (50 mL) suspension of potassium carbonate (6.2 g) was added dropwise DMF (70 mL) solution of $N^\alpha$-tert-butoxycarbonyl-1-formyl-L-tryptophan (10.0 g) at 0° C., and the mixture was stirred for 1 hour at room temperature. Next, DMF (25 mL) solution of iodomethane (2.8 mL) was added dropwise at 0° C., and the mixture was stirred for 20 hours at room temperature. The reaction mixture was poured into ice water and extracted with ethyl acetate. The organic layer was dried over anhydrous sodium sulfate, and thereafter the residue obtained by distilling off the solvent under a reduced pressure was purified with silica gel column chromatography (BZ-127ZH, n-hexane:ethyl acetate=7:3), to give the captioned compound (9.0 g, 86%) as crystals.

Example 29

Production of Methyl 1-Formyl-L-Tryptophanate Hydrochloride

To methylene chloride (200 mL) solution of the compound obtained in Example 28 (8.9 g, 25.7 mmol) was added dropwise 4 mol/L of hydrogen chloride-dioxane (19 mL) at room temperature, and the mixture was allowed to stir for 15 hours.

The crystals precipitated were filtered, and washed with diethyl ether, to give the captioned compound (7.2 g, 99%).

Example 30

Production of Methyl N$^\alpha$-[3-(2-Fluorophenyl)acryloyl]-1-Formyl-L-Tryptophanate The same procedures as in Example 2 were carried out from the compound obtained in Example 29 (4.0 g), triethylamine (2.2 mL), 2-fluorocinnamic acid (2.6 g), WSC.HCl (3.0 g), and methylene chloride (100 mL), to give the captioned compound (4.8 g, 86%) as an oily product.

Example 31

Production of Methyl N$^\alpha$-[3-(2-Fluorophenyl)acryloyl]-D-Tryptophanate

The same procedures as in Example 2 were carried out from methyl D-tryptophanate hydrochloride (2.5 g), triethylamine (1.6 mL), 2-fluorocinnamic acid (2.0 g), WSC.HCl (2.3 g), and methylene chloride (80 mL), to give the captioned compound (3.1 g, 86%) as an oily product.

Example 32

Production of Methyl N-tert-Butoxycarbonyl-O$^4$-Methyl-L-Tyrosinate

The same procedures as in Example 28 were carried out from N-tert-butoxycarbonyl-L-tyrosine (50.0 g), iodomethane (28 mL), potassium carbonate (62.0 g), and DMF (500 mL), to give the captioned compound (50.7 g, 92%) as an oily product.

Example 33

Production of Methyl O$^4$-Methyl-L-Tyrosinate Hydrochloride

The same procedures as in Example 29 were carried out from the compound obtained in Example 32 (50.6 g), 4 mol/L of hydrogen chloride-dioxane (123 mL), and methylene chloride (400 mL), to give the captioned compound (33.7 g, 84%) as crystals.

Example 34

Production of Methyl N-Acryloyl-O$^4$-Methyl-L-Tyrosinate

The same procedures as in Example 1 were carried out from the compound obtained in Example 33 (3.3 g), acrylic acid (1.1 mL), DCC (3.4 g), triethylamine (9.5 mL, 68.2 mmol), and chloroform (140 mL), to give the captioned compound (2.1 g, 58%) as crystals.

Example 35

Production of Methyl N-[3-(2-Acetoxyphenyl)acryloyl]-O$^4$-Methyl-L-Tyrosinate

The same procedures as in Example 2 were carried out from the compound obtained in Example 33 (8.0 g), triethylamine (5.4 mL), 2-acetoxycinnamic acid (8.1 g), WSC.HCl (7.5 g), and methylene chloride (200 mL), to give the captioned compound (8.8 g, 68%) as crystals.

Example 36

Production of Methyl N-[3-(3-Acetoxyphenyl)acryloyl]-O$^4$-Methyl-L-Tyrosinate

The same procedures as in Example 2 were carried out from the compound obtained in Example 33 (2.0 g), triethylamine (1.4 mL), 3-acetoxycinnamic acid (2.0 g), WSC.HCl (1.9 g), and methylene chloride (60 mL), to give the captioned compound (3.1 g, 96%) as an oily product.

Example 37

Production of Methyl N-[3-(4-Acetoxyphenyl)acryloyl]-O$^4$-Methyl-L-Tyrosinate

The same procedures as in Example 2 were carried out from the compound obtained in Example 33 (2.0 g), triethylamine (1.4 mL), 4-acetoxycinnamic acid (2.0 g), WSC.HCl (1.9 g), and methylene chloride (60 mL), to give the captioned compound (2.6 g, 79%) as crystals.

Example 38

Production of Methyl N-[3-(2-Fluorophenyl)acryloyl]-O$^4$-Methyl-L-Tyrosinate

The same procedures as in Example 2 were carried out from the compound obtained in Example 33 (4.8 g), triethylamine (3.3 mL), 2-fluorocinnamic acid (3.9 g), WSC.HCl (4.5 g), and methylene chloride (150 mL), to give the captioned compound (6.0 g, 86%) as crystals.

Example 39

Production of Methyl N-[3-(3-Fluorophenyl)acryloyl]-O$^4$-Methyl-L-Tyrosinate

The same procedures as in Example 2 were carried out from the compound obtained in Example 33 (2.0 g), triethylamine (1.4 mL), 3-fluorocinnamic acid (1.6 g), WSC.HCl (1.9 g), and methylene chloride (60 mL), to give the captioned compound (2.9 g, 99%) as an oily product.

Example 40

Production of Methyl N-[3-(4-Fluorophenyl)acryloyl]-O$^4$-Methyl-L-Tyrosinate

The same procedures as in Example 2 were carried out from the compound obtained in Example 33 (2.5 g), triethylamine (3.1 mL), 4-fluorocinnamic acid (1.9 g), WSC.HCl (2.1 g), and methylene chloride (100 mL), to give the captioned compound (2.5 g, 69%) as an amorphous solid product.

Example 41

Production of Methyl O$^4$-Methyl-N-(3-Phenylacryloyl)-L-Tyrosinate

The same procedures as in Example 2 were carried out from the compound obtained in Example 33 (2.5 g), triethylamine (3.1 mL), cinnamic acid (1.7 g), WSC.HCl (2.1 g), and methylene chloride (100 mL), to give the captioned compound (1.0 g, 29%) as an oily product.

Example 42

Production of Methyl N-[3-(2-Cyanophenyl)acryloyl]-O$^4$-Methyl-L-Tyrosinate

The same procedures as in Example 2 were carried out from the compound obtained in Example 33 (2.5 g), triethylamine (1.7 mL), 2-cyanocinnamic acid (2.1 g), WSC.HCl (2.3 g), and methylene chloride (70 mL), to give the captioned compound (3.2 g, 86%) as crystals.

Example 43

Production of Methyl O$^4$-Methyl-N-[3-(2-Trifluoromethylphenyl)acryloyl]-L-Tyrosinate The same procedures as in Example 2 were carried out from the compound obtained in Example 33 (2.5 g), triethylamine (1.7 mL), 2-trifluoromethylcinnamic acid (2.6 g), WSC.HCl (2.3 g), and methylene chloride (70 mL), to give the captioned compound (4.1 g, 99%) as an amorphous solid product.

Example 44

Production of Methyl N-[3-(2-Methoxyphenyl)acryloyl]-O$^4$-Methyl-L-Tyrosinate

The same procedures as in Example 2 were carried out from the compound obtained in Example 33 (2.5 g), triethylamine (3.1 mL), 2-methoxycinnamic acid (2.0 g), WSC.HCl (2.1 g), and methylene chloride (100 mL), to give the captioned compound (2.8 g, 76%) as an amorphous solid product.

Example 45

Production of Methyl N-[3-(2-Chlorophenyl)acryloyl]-O$^4$-Methyl-L-Tyrosinate

The same procedures as in Example 2 were carried out from the compound obtained in Example 33 (2.5 g), triethylamine (1.7 mL), 2-chlorocinnamic acid (2.2 g), WSC.HCl (2.3 g), and methylene chloride (70 mL), to give the captioned compound (2.9 g, 76%) as crystals.

Example 46

Production of Methyl N-[3-(2,6-Difluorophenyl) acryloyl]-O$^4$-Methyl-L-Tyrosinate The same procedures as in Example 2 were carried out from the compound obtained in Example 33 (2.5 g), triethylamine (1.7 mL), 2,6-difluorocinnamic acid (2.2 g), WSC.HCl (2.3 g), and methylene chloride (70 mL), to give the captioned compound (3.1 g, 82%) as crystals.

Example 47

Production of Methyl N-[3-(2,4-Difluorophenyl) acryloyl]-O$^4$-Methyl-L-Tyrosinate The same procedures as in Example 2 were carried out from the compound obtained in Example 33 (2.5 g), triethylamine (1.7 mL), 2,4-difluorocinnamic acid (2.2 g), WSC.HCl (2.3 g), and methylene chloride (70 mL), to give the captioned compound (3.0 g, 80%) as crystals.

Example 48

Production of Methyl N-[3-(2,5-Difluorophenyl) acryloyl]-O$^4$-Methyl-L-Tyrosinate The same procedures as in Example 2 were carried out from the compound obtained in Example 33 (2.5 g), triethylamine (1.7 mL), 2,5-difluorocinnamic acid (2.2 g), WSC.HCl (2.3 g), and methylene chloride (70 mL), to give the captioned compound (2.8 g, 74%) as crystals.

Example 49

Production of Methyl N-{3-[3,5-Bis(trifluoromethyl) phenyl]acryloyl}-O$^4$-Methyl-L-Tyrosinate The same procedures as in Example 2 were carried out from the compound obtained in Example 33 (2.5 g), triethylamine (1.7 mL), 3,5-bis(trifluoromethyl)cinnamic acid (3.5 g), WSC.HCl (2.3 g), and methylene chloride (70 mL), to give the captioned compound (3.4 g, 70%) as an oily product.

Example 50

Production of Methyl O$^4$-Methyl-N43-(4-Phenoxyphenyl)acryloyl]-L-Tyrosinate

The same procedures as in Example 2 were carried out from the compound obtained in Example 33 (2.5 g), triethylamine (1.7 mL), 4-phenoxycinnamic acid (2.9 g), WSC.HCl (2.3 g), and methylene chloride (70 mL), to give the captioned compound (3.3 g, 74%) as crystals.

Example 51

Production of Methyl N-(Benzofuran-2-Carbonyl)-O$^4$-Methyl-L-Tyrosinate

The same procedures as in Example 2 were carried out from the compound obtained in Example 33 (2.5 g), triethylamine (1.7 mL), benzofuran-2-carboxylic acid (2.0 g), WSC.HCl (2.3 g), and methylene chloride (70 mL), to give the captioned compound (3.4 g, 96%) as an oily product.

Example 52

Production of Methyl N-(Coumarin-3-Carbonyl)-O$^4$-Methyl-L-Tyrosinate

The same procedures as in Example 2 were carried out from the compound obtained in Example 33 (2.5 g), triethylamine (1.7 mL), coumarin-3-carboxylic acid (2.3 g), WSC.HCl (2.3 g), and methylene chloride (70 mL), to give the captioned compound (2.8 g, 71%) as crystals.

Example 53

Production of Methyl N-[3-(2-Fluorophenyl)acryloyl]-L-Leucinate

The same procedures as in Example 2 were carried out from methyl L-leucinate hydrochloride (3.0 g), triethylamine (2.5 mL), 2-fluorocinnamic acid (3.0 g), WSC.HCl (3.5 g), and methylene chloride (100 mL), to give the captioned compound (4.3 g, 88%) as crystals.

Example 54

Production of Methyl
N-[3-(2-Fluorophenyl)acryloyl]-L-Serinate

The same procedures as in Example 2 were carried out from methyl L-serinate hydrochloride (2.5 g), triethylamine (2.4 mL), 2-fluorocinnamic acid (2.8 g), WSC.HCl (3.2 g), and methylene chloride (100 mL), to give the captioned compound (4.2 g, 98%) as an oily product.

Example 55

Production of Methyl
N-[3-(2-Fluorophenyl)acryloyl]-L-Methioninate

The same procedures as in Example 2 were carried out from methyl L-methioninate hydrochloride (2.5 g), triethylamine (2.1 mL), 2-fluorocinnamic acid (2.5 g), WSC.HCl (2.9 g, 15.0 mmol), and methylene chloride (80 mL), to give the captioned compound (3.7 g, 95%) as an oily product.

Example 56

Production of Diethyl
N-[3-(2-Fluorophenyl)acryloyl]-L-Glutaminate

The same procedures as in Example 2 were carried out from diethyl L-glutaminate (4.0 g), triethylamine (5.2 mL), 2-fluorocinnamic acid (3.1 g), WSC.HCl (3.5 g), and methylene chloride (150 mL), to give the captioned compound (4.0 g, 68%) as an amorphous solid product.

Example 57

Production of Methyl $N^{\alpha}$-[3-(2-Fluorophenyl)acryloyl]-$N^{\delta}$-tert-Butoxycarbonyl-L-Ornithinate The same procedures as in Example 2 were carried out from methyl $N^{\alpha}$-tert-butoxycarbonyl-L-ornithinate hydrochloride (5.0 g), triethylamine (3.0 mL), 2-fluorocinnamic acid (3.1 g), WSC.HCl (4.1 g), and methylene chloride (100 mL), to give the captioned compound (6.9 g, 99%) as an oily product.

Example 58

Production of Methyl $N^{\alpha}$-[3-(2-Fluorophenyl)acryloyl]-$N^{\epsilon}$-tert-Butoxycarbonyl-L-Lysinate The same procedures as in Example 2 were carried out from methyl $N^{\omega}$-tert-butoxycarbonyl-L-lysinate hydrochloride (10.0 g), triethylamine (5.6 mL), 2-fluorocinnamic acid (6.7 g), WSC.HCl (7.7 g), and methylene chloride (200 mL), to give the captioned compound (10.2 g, 74%) as crystals.

Example 59

Production of Methyl $N^{\alpha}$-[3-(2-Fluorophenyl)acryloyl]-$N^{\omega}$-(2,2,4,6,7-Pentamethyldihydrobenzofuran-5-Sulfonyl)-L-Argininate.

The same procedures as in Example 2 were carried out from methyl $N^{\omega}$-(2,2,4,6,7-pentamethyldihydrobenzofuran-5-sulfonyl)-L-argininate hydrochloride (5.0 g), triethylamine (1.8 mL), 2-fluorocinnamic acid (2.1 g), WSC.HCl (2.4 g), and methylene chloride (150 mL), to give the captioned compound (6.1 g, 99%) as an amorphous solid product.

Example 60

Production of Sodium $N^{\alpha}$-Acryloyl-L-Tryptophanate [Compound 1]

To methanol (50 mL) solution of the compound obtained in Example 1 (1.0 g, 3.7 mmol) was added l mol/L of an aqueous sodium hydroxide solution (5.6 mL) at room temperature. The mixture was allowed to stir for 2 hours, and thereafter to the residue obtained by distilling off the solvent under reduced pressure was added water, and the pH of the solution was adjusted to about pH 7 with polystyrene bound type p-toluensulfonate beads (2.8 mmol/g) (2.0 g), Beads were filtered off with a Millipore filter, thereafter the filtrate was distilled off under a reduced pressure, and the crystals precipitated were filtered with diethyl ether, to give the captioned compound (0.9 g, 87%).

Example 61

Production of Sodium $N^{\alpha}$-[3-(2-Hydroxyphenyl)acryloyl]-L-Tryptophanate [Compound 2]

The same procedures as in Example 60 were carried out from the compound obtained in Example 2 (5.0 g), 1 mol/L of an aqueous sodium hydroxide solution (37 mL), and methanol (300 mL), to give the captioned compound (4.3 g, 94%) as crystals.

Example 62

Production of Sodium $N^{\alpha}$-[3-(3-Hydroxyphenyl)acryloyl]-L-Tryptophanate [Compound 6]

The same procedures as in Example 60 were carried out from the compound obtained in Example 3 (4.7 g), 1 mol/L of an aqueous sodium hydroxide solution (35 mL), and methanol (300 mL), to give the captioned compound (2.8 g, 65%) as crystals.

Example 63

Production of Sodium $N^{\alpha}$-[3-(4-Hydroxyphenyl)acryloyl]-L-Tryptophanate [Compound 7]

The same procedures as in Example 60 were carried out from the compound obtained in Example 4 (4.5 g), 1 mol/L of an aqueous sodium hydroxide solution (33 mL), and methanol (300 mL), to give the captioned compound (3.7 g, 90%) as crystals.

Example 64

Production of $N^{\alpha}$-[3-(2-Fluorophenyl)acryloyl]-L-Tryptophan [Compound 3]

To methanol (290 mL) solution of the compound obtained in Example 5 (7.1 g) was added dropwise 1 mol/L of an aqueous sodium hydroxide solution (29 mL) at room temperature. The mixture was allowed to stir for 29 hours, and thereafter to the residue obtained by distilling off the solvent under a reduced pressure was added water. The solution was made acidic with dilute hydrochloric acid, and the crystals precipitated were filtered, to give the captioned compound (5.4 g, 79%).

Example 65

Production of Sodium N$^\alpha$-[3-(3-Fluorophenyl)acryloyl]-L-Tryptophanate [Compound 4]

The same procedures as in Example 60 were carried out from the compound obtained in Example 6 (4.2 g), 1 mol/L of an aqueous sodium hydroxide solution (17 mL), and methanol (170 mL), to give the captioned compound (3.7 g, 86%) as an amorphous solid product.

Example 66

Production of Sodium N$^\alpha$-[3-(4-Fluorophenyl)acryloyl]-L-Tryptophanate [Compound 5]

The same procedures as in Example 60 were carried out from the compound obtained in Example 7 (3.0 g), 1 mol/L of an aqueous sodium hydroxide solution (35 mL), and methanol (150 mL), to give the captioned compound (3.0 g, 98%) as crystals.

Example 67

Production of Sodium N$^\alpha$-(3-Phenylacryloyl)-L-Tryptophanate [Compound 8]

The same procedures as in Example 60 were carried out from the compound obtained in Example 8 (3.7 g), 1 mol/L of an aqueous sodium hydroxide solution (32 mL), and methanol (150 mL), to give the captioned compound (3.7 g, 98%) as crystals.

Example 68

Production of Sodium N$^\alpha$-[3-(2-Cyanophenyl)acryloyl]-L-Tryptophanate [Compound 9]

The same procedures as in Example 60 were carried out from the compound obtained in Example 9 (5.8 g), 1 mol/L of an aqueous sodium hydroxide solution (23 mL), and methanol (200 mL), to give the captioned compound (4.3 g, 73%) as crystals.

Example 69

Production of Sodium N$^\alpha$-[3-(2-Trifluoromethylphenyl)acryloyl]-L-Tryptophanate [Compound 10]

The same procedures as in Example 60 were carried out from the compound obtained in Example 10 (3.4 g), 1 mol/L of an aqueous sodium hydroxide solution (12 mL), and methanol (120 mL), to give the captioned compound (1.6 g, 46%) as crystals.

Example 70

Production of Sodium N$^\alpha$-[3-(2-Methoxyphenyl)acryloyl]-L-Tryptophanate [Compound 11]

The same procedures as in Example 60 were carried out from the compound obtained in Example 11 (5.2 g), 1 mol/L of an aqueous sodium hydroxide solution (42 mL), and methanol (150 mL), to give the captioned compound (2.9 g, 55%) as crystals.

Example 71

Production of N$^\alpha$-[3-(2-Chlorophenyl)acryloyl]-L-Tryptophan [Compound 12]

The same procedures as in Example 64 were carried out from the compound obtained in Example 12 (4.5 g), 1 mol/L of an aqueous sodium hydroxide solution (18 mL), and methanol (180 mL), to give the captioned compound (3.7 g, 85%) as crystals.

Example 72

Production of Sodium N$^\alpha$-[3-(2,6-Difluorophenyl)acryloyl]-L-Tryptophanate [Compound 13]

The same procedures as in Example 60 were carried out from the compound obtained in Example 13 (3.9 g), 1 mol/L of an aqueous sodium hydroxide solution (15 mL), and methanol (150 mL), to give the captioned compound (2.7 g, 68%) as an amorphous solid product.

Example 73

Production of Sodium N$^\alpha$-[3-(2,4-Difluorophenyl)acryloyl]-L-Tryptophanate [Compound 14]

The same procedures as in Example 60 were carried out from the compound obtained in Example 14 (4.5 g), 1 mol/L of an aqueous sodium hydroxide solution (18 mL), and methanol (180 mL), to give the captioned compound (4.1 g, 89%) as an amorphous solid product.

Example 74

Production of N$^\alpha$-[3-(2,5-Difluorophenyl)acryloyl]-L-Tryptophan [Compound 15]

The same procedures as in Example 64 were carried out from the compound obtained in Example 15 (4.1 g), 1 mol/L of an aqueous sodium hydroxide solution (16 mL), and methanol (160 mL), to give the captioned compound (3.9 g, 99%) as crystals.

Example 75

Production of N$^\alpha$-{3-[3,5-Bis(trifluoromethyl)phenyl]acryloyl}-L-Tryptophan [Compound 16]

The same procedures as in Example 64 were carried out from the compound obtained in Example 16 (2.6 g), 1 mol/L of an aqueous sodium hydroxide solution (8.0 mL), and methanol (80 mL), to give the captioned compound (2.1 g, 83%) as crystals.

Example 76

Production of N$^\alpha$-[3-(4-Phenoxyphenyl)acryloyl]-L-Tryptophan [Compound 18]

The same procedures as in Example 64 were carried out from the compound obtained in Example 17 (4.9 g), 1 mol/L of an aqueous sodium hydroxide solution (17 mL), and methanol (170 mL), to give the captioned compound (4.2 g, 89%) as crystals.

Example 77

Production of $N^\alpha$-(Benzofuran-2-Carbonyl)-L-Tryptophan [Compound 20]

The same procedures as in Example 64 were carried out from the compound obtained in Example 18 (5.6 g), 1 mol/L of an aqueous sodium hydroxide solution (23 mL), and methanol (230 mL), to give the captioned compound (3.7 g, 69%) as crystals.

Example 78

Production of $N^\alpha$-(Coumarin-3-Carbonyl)-L-Tryptophan [Compound 21]

The same procedures as in Example 64 were carried out from the compound obtained in Example 19 (2.0 g), 1 mol/L of an aqueous sodium hydroxide solution (7.7 mL), and methanol (80 mL), to give the captioned compound (1.9 g, 99%) as crystals.

Example 79

Production of $N^\alpha$-[3-(2-Hydroxyphenyl)acryloyl]-1-Methyl-L-Tryptophan [Compound 26]

The same procedures as in Example 64 were carried out from the compound obtained in Example 21 (3.9 g), 1 mol/L of an aqueous sodium hydroxide solution (28 mL), and methanol (140 mL), to give the captioned compound (2.1 g, 62%) as crystals.

Example 80

Production of $N^\alpha$-[3-(2-Fluorophenyl)acryloyl]-1-Methyl-L-Tryptophan [Compound 27]

The same procedures as in Example 64 were carried out from the compound obtained in Example 22 (3.1 g), 1 mol/L of an aqueous sodium hydroxide solution (12 mL), and methanol (120 mL), to give the captioned compound (2.5 g, 85%) as crystals.

Example 81

Production of $N^\alpha$-[3-(4-Fluorophenyl)acryloyl]-1-Methyl-L-Tryptophan [Compound 28]

The same procedures as in Example 64 were carried out from the compound obtained in Example 23 (2.7 g), 1 mol/L of an aqueous sodium hydroxide solution (10.5 mL), and methanol (110 mL), to give the captioned compound (2.1 g, 80%) as crystals.

Example 82

Production of $N^\alpha$-[3-(2,6-Difluorophenyl)acryloyl]-1-Methyl-L-Tryptophan [Compound 31]

The same procedures as in Example 64 were carried out from the compound obtained in Example 24 (1.1 g), 1 mol/L of an aqueous sodium hydroxide solution (4.0 mL), and methanol (40 mL), to give the captioned compound (0.76 g, 74%) as crystals.

Example 83

Production of $N^\alpha$-[3-(2,4-Difluorophenyl)acryloyl]-1-Methyl-L-Tryptophan [Compound 32]

The same procedures as in Example 64 were carried out from the compound obtained in Example 25 (0.73 g), 1 mol/L of an aqueous sodium hydroxide solution (2.7 mL), and methanol (27 mL), to give the captioned compound (0.54 g, 77%) as crystals.

Example 84

Production of $N^\alpha$-[3-(2,5-Difluorophenyl)acryloyl]-1-Methyl-L-Tryptophan [Compound 33]

The same procedures as in Example 64 were carried out from the compound obtained in Example 26 (2.9 g), 1 mol/L of an aqueous sodium hydroxide solution (15.0 mL), and methanol (150 mL), to give the captioned compound (2.1 g, 74%) as crystals.

Example 85

Production of 1-Methyl-$N^\alpha$-[3-(4-Phenoxyphenyl)acryloyl]-L-Tryptophan [Compound 35]

The same procedures as in Example 64 were carried out from the compound obtained in Example 27 (0.93 g), 1 mol/L of an aqueous sodium hydroxide solution (3.1 mL), and methanol (30 mL), to give the captioned compound (0.81 g, 90%) as crystals.

Example 86

Production of $N^\alpha$-[3-(2-Fluorophenyl)acryloyl]-1-Formyl-L-Tryptophan [Compound 68]

The same procedures as in Example 64 were carried out from the compound obtained in Example 30 (4.8 g), 1 mol/L of an aqueous sodium hydroxide solution (16 mL), and methanol (160 mL), to give the captioned compound (3.5 g, 75%) as crystals.

Example 87

Production of $N^\alpha$-[3-(2-Fluorophenyl)acryloyl]-D-Tryptophan "Compound 24]

The same procedures as in Example 64 were carried out from the compound obtained in Example 31 (3.1 g), 1 mol/L of an aqueous sodium hydroxide solution (13 mL), and methanol (130 mL), to give the captioned compound (2.8 g, 95%) as crystals.

Example 88

Production of Sodium N-Acryloyl-$O^4$-Methyl-L-Tyrosinate [Compound 38]

The same procedures as in Example 60 were carried out from the compound obtained in Example 34 (1.9 g), 1 mol/L

Example 89

Production of N-[3-(2-Hydroxyphenyl)acryloyl]-$O^4$-Methyl-L-Tyrosine [Compound 39]

The same procedures as in Example 64 were carried out from the compound obtained in Example 35 (6.0 g), 1 mol/L of an aqueous sodium hydroxide solution (38 mL), and methanol (300 mL), to give the captioned compound (4.4 g, 85%) as an amorphous solid product.

Example 90

Production of N-[3-(3-Hydroxyphenyl)acryloyl]-$O^4$-Methyl-L-Tyrosine [Compound 43]

To methanol (240 mL) solution of the compound obtained in Example 36 (3.1 g) was added dropwise 1 mol/L of an aqueous sodium hydroxide solution (24 mL) at room temperature, and the mixture was allowed to stir for 17 hours. To the residue obtained by distilling off the solvent under a reduced pressure was added water, and the mixture was made acidic with dilute hydrochloric acid, and thereafter extracted with ethyl acetate. The organic layer was washed with saturated sodium chloride solution, and dried over anhydrous sodium sulfate. The solvent was distilled off under a reduced pressure, to give the captioned compound (1.4 g, 51%) as an amorphous solid product.

Example 91

Production of N-[3-(4-Hydroxyphenyl)acryloyl]-$O^4$-Methyl-L-Tyrosine [Compound 44]

The same procedures as in Example 90 were carried out from the compound obtained in Example 37 (2.5 g), 1 mol/L of an aqueous sodium hydroxide solution (19 mL), and methanol (190 mL), to give the captioned compound (1.2 g, 57%) as an amorphous solid product.

Example 92

Production of N-[3-(2-Fluorophenyl)acryloyl]-$O^4$-Methyl-L-Tyrosine [Compound 40]

The same procedures as in Example 90 were carried out from the compound obtained in Example 38 (5.8 g), 1 mol/L of an aqueous sodium hydroxide solution (24 mL), and methanol (200 mL), to give the captioned compound (4.2 g, 76%) as crystals.

Example 93

Production of N-[3-(3-Fluorophenyl)acryloyl]-$O^4$-Methyl-L-Tyrosine [Compound 41]

The same procedures as in Example 90 were carried out from the compound obtained in Example 39 (2.9 g), 1 mol/L of an aqueous sodium hydroxide solution (12 mL), and methanol (120 mL), to give the captioned compound (1.7 g, 61%) as crystals.

Example 94

Production of N-[3-(4-Fluorophenyl)acryloyl]-$O^4$-Methyl-L-Tyrosine [Compound 42]

The same procedures as in Example 90 were carried out from the compound obtained in Example 40 (2.5 g), 1 mol/L of an aqueous sodium hydroxide solution (21 mL), and methanol (150 mL), to give the captioned compound (2.2 g, 90%) as crystals.

Example 95

Production of $O^4$-Methyl-N-(3-Phenylacryloyl)-L-Tyrosine [Compound 45]

The same procedures as in Example 90 were carried out from the compound obtained in Example 41 (3.4 g), 1 mol/L of an aqueous sodium hydroxide solution (19 mL), and methanol (150 mL), to give the captioned compound (2.0 g, 62%) as crystals.

Example 96

Production of N-[3-(2-Cyanophenyl)acryloyl]-$O^4$-Methyl-L-Tyrosine [Compound 46]

The same procedures as in Example 64 were carried out from the compound obtained in Example 42 (3.1 g), 1 mol/L of an aqueous sodium hydroxide solution (13 mL), and methanol (130 mL), to give the captioned compound (2.7 g, 89%) as crystals.

Example 97

Production of $O^4$-Methyl-N-[3-(2-Trifluoromethylphenyl)acryloyl]-L-Tyrosine [Compound 47]

The same procedures as in Example 64 were carried out from the compound obtained in Example 43 (4.1 g), 1 mol/L of an aqueous sodium hydroxide solution (15 mL), and methanol (150 mL), to give the captioned compound (3.3 g, 83%) as crystals.

Example 98

Production of N-[3-(2-Methoxyphenyl)acryloyl]-$O^4$-Methyl-L-Tyrosine [Compound 48]

The same procedures as in Example 90 were carried out from the compound obtained in Example 44 (1.6 g), 1 mol/L of an aqueous sodium hydroxide solution (13 mL), and methanol (150 mL), to give the captioned compound (1.2 g, 75%) as crystals.

Example 99

Production of N-[3-(2-Chlorophenyl)acryloyl]-$O^4$-Methyl-L-Tyrosine [Compound 49]

The same procedures as in Example 64 were carried out from the compound obtained in Example 45 (2.9 g), 1 mol/L of an aqueous sodium hydroxide solution (12 mL), and methanol (120 mL), to give the captioned compound (2.4 g, 79%) as crystals.

of an aqueous sodium hydroxide solution (11 mL), and methanol (70 mL), to give the captioned compound (1.9 g, 97%) as crystals.

Example 100

Production of N-[3-(2,6-Difluorophenyl)acryloyl]-O$^4$-Methyl-L-Tyrosine [Compound 50]

The same procedures as in Example 64 were carried out from the compound obtained in Example 46 (3.0 g), 1 mol/L of an aqueous sodium hydroxide solution (12 mL), and methanol (120 mL), to give the captioned compound (2.8 g, 95%) as crystals,

Example 101

Production of N-[3-(2,4-Difluorophenyl)acryloyl]-O$^4$-Methyl-L-Tyrosine [Compound 51]

The same procedures as in Example 64 were carried out from the compound obtained in Example 47 (2.9 g), 1 mol/L of an aqueous sodium hydroxide solution (12 mL), and methanol (120 mL), to give the captioned compound (2.7 g, 96%) as crystals.

Example 102

Production of N-[3-(2,5-Difluorophenyl)acryloyl]-O$^4$-Methyl-L-Tyrosine [Compound 52]

The same procedures as in Example 64 were carried out from the compound obtained in Example 48 (2.8 g), 1 mol/L of an aqueous sodium hydroxide solution (11 mL), and methanol (110 mL), to give the captioned compound (2.4 g, 89%) as crystals.

Example 103

Production of N-{3-[3,5-Bis(trifluoromethyl)phenyl]acryloyl}-O$^4$-Methyl-L-Tyrosine [Compound 53]

The same procedures as in Example 90 were carried out from the compound obtained in Example 49 (3.4 g), 1 mol/L of an aqueous sodium hydroxide solution (11 mL), and methanol (110 mL), to give the captioned compound (2.3 g, 71%) as crystals.

Example 104

Production of O$^4$-Methyl-N-[3-(4-Phenoxyphenylacryloyl)]-L-Tyrosine [Compound 55]

The same procedures as in Example 64 were carried out from the compound obtained in Example 50 (3.2 g), 1 mol/L of an aqueous sodium hydroxide solution (11 mL), and methanol (110 mL), to give the captioned compound (3.1 g, 99%) as crystals.

Example 105

Production of N-(Benzofuran-2-Carbonyl)-O$^4$-Methyl-L-Tyrosine [Compound 57]

The same procedures as in Example 64 were carried out from the compound obtained in Example 51 (3.4 g), 1 mol/L of an aqueous sodium hydroxide solution (15 mL), and methanol (150 mL), to give the captioned compound (2.6 g, 78%) as crystals.

Example 106

Production of N-(Coumarin-3-Carbonyl)-O$^4$-Methyl-L-Tyrosine [Compound 58]

The same procedures as in Example 90 were carried out from the compound obtained in Example 52 (2.7 g), 1 mol/L of an aqueous sodium hydroxide solution (11 mL), and methanol (110 mL), to give the captioned compound (2.1 g, 80%) as crystals.

Example 107

Production of N-[3-(2-Fluorophenyl)acryloyl]-L-Leucine [Compound 59]

The same procedures as in Example 64 were carried out from the compound obtained in Example 53 (4.0 g), 1 mol/L of an aqueous sodium hydroxide solution (21 mL), and methanol (200 mL), to give the captioned compound (3.6 g, 93%) as an amorphous solid product.

Example 108

Production of N-[3-(2-Fluorophenyl)acryloyl]-L-Serine [Compound 66]

The same procedures as in Example 64 were carried out from the compound obtained in Example 54 (4.2 g), 1 mol/L of an aqueous sodium hydroxide solution (39 mL), and methanol (390 mL), to give the captioned compound (2.9 g, 73%) as crystals.

Example 109

Production of N-[3-(2-Fluorophenyl)acryloyl]-L-Methionine [Compound 67]

The same procedures as in Example 64 were carried out from the compound obtained in Example 55 (3.7 g), 1 mol/L of an aqueous sodium hydroxide solution (18 mL), and methanol (180 mL), to give the captioned compound (3.0 g, 85%) as crystals.

Example 110

Production of Disodium N-[3-(2-Fluorophenyl)acryloyl]-L-Glutaminate [Compound 60]

The same procedures as in Example 60 were carried out from the compound obtained in Example 56 (4.0 g), 1 mol/L of an aqueous sodium hydroxide solution (34 mL), and methanol (150 mL), to give the captioned compound (2.4 g, 62%) as crystals.

Example 111

Production of N$^\alpha$-[3-(2-Fluorophenyl)acryloyl]-N$^\delta$-tert-Butoxycarbonyl-L-Ornithine To methanol (260 mL) of the compound obtained in Example 57 (6.9 g) was added dropwise 1 mol/L of an aqueous sodium hydroxide solution (26 mL) at room temperature, and the mixture was allowed to stir for 21 hours. To the residue obtained by distilling off the solvent under a reduced pressure was added water, and the mixture was made acidic with 10% citric acid. The solution was extracted with ethyl acetate and thereafter the organic layer was washed with saturated sodium chloride solution, and dried over anhydrous sodium sulfate. The solvent was distilled off under a reduced pressure, to give the captioned compound (5.4 g, 81%) as an oily product.

Example 112

Production of $N^\alpha$-[3-(2-Fluorophenyl)acryloyl]-L-Ornithinate Hydrochloride [Compound 63]

The same procedures as in Example 29 were carried out from the compound obtained in Example 111 (5.4 g), 4 mol/L of hydrogen chloride-dioxane (11 mL), and methylene chloride (200 mL), to give the captioned compound (4.1 g, 90%) as crystals.

Example 113

Production of $N^\alpha$-[3-(2-Fluorophenyl)acryloyl]-$N^\epsilon$-tert-Butoxycarbonyl-L-Lysine The same procedures as in Example 111 were carried out from the compound obtained in Example 58 (4.0 g), 1 mol/L of an aqueous sodium hydroxide solution (16 mL), and methanol (160 mL), to give the captioned compound (3.8 g, 98%) as an oily product.

Example 114

Production of $N^\alpha$-[3-(2-Fluorophenyl)acryloyl]-L-Lysinate Hydrochloride [Compound 61]

The same procedures as in Example 29 were carried out from the compound obtained in Example 113 (3.8 g), 4 mol/L of hydrogen chloride-dioxane (7.0 mL), and methylene chloride (80 mL), to give the captioned compound (3.0 g, 92%) as crystals.

Example 115

Production of $N^\alpha$-[3-(2-Fluorophenyl)acryloyl]-$N^\omega$-(2,2,4,6,7-Pentamethyldihydrobenzofuran-5-sulfonyl)-L-Arginine The same procedures as in Example 111 were carried out from the compound obtained in Example 59 (3.2 g), 1 mol/L of an aqueous sodium hydroxide solution (8.0 mL), and methanol (80 mL), to give the captioned compound (2.8 g, 91%) as an oily product.

Example 116

Production of $N^\alpha$-[3-(2-Fluorophenyl)acryloyl]-L-Arginine [Compound 64]

To methylene chloride solution of the compound obtained in Example 115 (2.8 g) was added dropwise trifluoroacetic acid (50 mL) at room temperature, and the mixture was allowed to stir for 24 hours. To the residue obtained by distilling off the solvent under a reduced pressure was added diethylether, and the mixture was stirred for 24 hours at room temperature. The crystals precipitated were filtered, to give the captioned compound (1.4 g, 68%).

Example 117

Production of 2,5-Dioxopyrrolidin-1-yl 3-(3-Cyanophenyl)Acrylate

To methylene chloride (300 mL) suspension of 3-cyanocinnamic acid (9.0 g) and N-hydroxysuccinic acid imide (9.0 g) was added WSC.HCl (15.0 g) at 0° C., and the mixture was stirred for 6 hours at room temperature. The reaction mixture was washed with water, and the organic layer was dried over anhydrous sodium sulfate. The crystals obtained by distilling off the solvent under a reduced pressure were filtered with diethyl ether, to give the captioned compound (13.0 g, 93%).

Example 118

Production of 2,5-Dioxopyrrolidin-1-yl 3-(4-Cyanophenyl)Acrylate

The same procedures as in Example 117 were carried out from 4-cyanocinnamic acid (5.0 g), N-hydroxysuccinic acid imide (5.0 g), WSC.HCl (8.3 g), and methylene chloride (150 mL), to give the captioned compound (6.2 g, 79%) as crystals.

Example 119

Production of 2,5-Dioxopyrrolidin-1-yl 2-Cyano-3-Phenyl Acrylate

To methylene chloride (300 mL) suspension of a-cyanocinnamic acid (10.0 g) and N-hydroxysuccinic acid imide (10.0 g) was added WSC.HCl (16.6 g) at 0° C., and the mixture was stirred for 22 hours at room temperature. The reaction mixture was washed with water, and the organic layer was dried over anhydrous sodium sulfate. The residue obtained by distilling off the solvent under a reduced pressure was purified with a silica gel column chromatography (chloroform), to give the captioned compound (6.9 g, 44%) as crystals.

Example 120

Production of 2,5-Dioxopyrrolidin-1-yl 2-Cyano-3-(2-Fluorophenyl)Acrylate

The same procedures as in Example 119 were carried out from α-cyano-2-fluorocinnamic acid (12.0 g), N-hydroxysuccinic acid imide (10.8 g), WSC.HCl (18.1 g), and methylene chloride (300 mL), to give the captioned compound (8.0 g, 44%) as crystals.

Example 121

Production of $N^\alpha$-[3-(3-Cyanophenyl)acryloyl]-L-Tryptophan [Compound 17]

To water (80 mL)-dioxane (80 mL) solution of L-tryptophan (3.0 g) was added sodium hydrogencarbonate (1.3 g) at 0° C., and the mixture was stirred for 30 minutes at room temperature. Next, dioxane (80 mL) solution of the compound obtained in Example 117 (4.2 g) was added to the mixture solution at 0° C., the mixture was stirred for 17 hours at room temperature. The reaction mixture was concentrated to a ⅓ volume under a reduced pressure, thereafter the solution was made acidic with a 10% aqueous citric acid solution, and the crystals precipitated were filtered. The crystals were washed with water, to give the captioned compound (4.6 g, 87%).

Example 122

Production of $N^\alpha$-[3-(4-Cyanophenyl)acryloyl]-L-Tryptophan [Compound 19]

The same procedures as in Example 121 were carried out from L-tryptophan (2.0 g), sodium hydrogencarbonate (0.9 g), the compound obtained in Example 118 (2.6 g), water (80 mL), and dioxane (160 mL), to give the captioned compound (1.9 g, 53%) as crystals.

Example 123

Production of $N^\alpha$-(2-Cyano-3-Phenylacryloyl)-L-Tryptophan [Compound 25]

The same procedures as in Example 121 were carried out from L-tryptophan (2.5 g), sodium hydrogencarbonate (1.1 g), the compound obtained in Example 119 (3.3 g), water (70 mL), and dioxane (150 mL), to give the captioned compound (1.3 g, 29%) as crystals.

Example 124

Production of $N^\alpha$-[2-Cyano-3-(2-Fluorophenyl)acryloyl]-L-Tryptophan [Compound 22]

The same procedures as in Example 121 were carried out from L-tryptophan (3.0 g), sodium hydrogencarbonate (1.3 g), the compound obtained in Example 120 (4.2 g), water (80 mL), and dioxane (160 mL), to give the captioned compound (2.5 g, 45%) as crystals.

Example 125

Production of $N^\alpha$-Benzyloxycarbonyl-L-Tryptophan Amide

To THF (150 mL) solution of $N^\alpha$-benzyloxycarbonyl-L-tryptophan-2,5-dioxopyrrolidin-1-yl ester (5.0 g) was added dropwise a 30% aqueous ammonia (3.3 mL) at 0° C., and thereafter the mixture was stirred for 2 hours at room temperature. The crystals were distilled off, and thereafter to the residue obtained by distilling off the solvent of the filtrate under a reduced pressure was added petroleum ether and a small amount of diethyl ether, and the crystals precipitated were filtered, to give the captioned compound (3.6 g, 91%).

Example 126

Production of L-Tryptophan Amide

To methanol (300 mL) solution of the compound obtained in Example 125 (3.6 g) was added 5% palladium/carbon (0.36 g) in an argon atmosphere, and the mixture was stirred for 16 hours at room temperature in a hydrogen atmosphere. The catalyst was filtered off, and the solvent was distilled off under a reduced pressure, to give the captioned compound (2.1 g, 95%) as an oily product.

Example 127

Production of $N^\alpha$-[3-(2-Fluorophenyl)acryloyl]-L-Tryptophan Amide [Compound 23]

To THF (80 mL) solution of 2,5-dioxopyrrolidin-1-yl 3-(2-fluorophenyl)acrylate (2.7 g) was added dropwise THF (80 mL) suspension of the compound 128 (2.1 g) at 0° C., and thereafter the mixture was stirred for 2 hours at room temperature. DMF (10 mL) was added thereto, and thereafter the mixture was further stirred at room temperature for 19 hours. To the residue obtained by distilling off the solvent under a reduced pressure was added ethyl acetate, the mixture was washed with water, and thereafter the organic layer was dried over anhydrous sodium sulfate. The residue obtained by distilling off the solvent under a reduced pressure was purified with silica gel column chromatography (BW-127ZH, chloroform:methanol=40:1), to give the captioned compound (1.6 g, 43%) as crystals.

Example 128

Production of 1-Methyl-$N^\alpha$-(3-phenylacryloyl)-L-Tryptophan [Compound 29]

The same procedures as in Example 121 were carried out from 1-methyl-L-tryptophan (2.0 g), sodium hydrogencarbonate (0.8 g), 2,5-dioxopyrrolidin-1-yl 3-phenyl acrylate (2.3 g), water (60 mL), and dioxane (140 mL), to give the captioned compound (1.1 g, 33%) as crystals.

Example 129

Production of $N^\alpha$-[3-(2-Cyanophenyl)acryloyl]-1-Methyl-L-Tryptophan [Compound 30]

To water (60 mL)-dioxane (60 mL) suspension of 1-methyl-L-tryptophan (2.1 g) was added sodium hydrogencarbonate (0.8 g) at 0° C., and the mixture was stirred for 30 minutes at room temperature. Dioxane (80 mL) solution of 2,5-dioxopyrrolidin-1-yl 3-(2-cyanophenyl)acrylate (2.5 g, 9.2 mmol) was added dropwise to the reaction mixture at 0° C., and the mixture was stirred for 15 hours at room temperature. The reaction mixture was concentrated to a ⅓ volume under a reduced pressure, water was added thereto, and the mixture was washed with diethyl ether. The aqueous layer was made acidic with a 10% aqueous citric acid solution, and thereafter extracted with ethyl acetate. The organic layer was washed with saturated sodium chloride solution, and thereafter dried over anhydrous sodium sulfate. The solvent was distilled off under a reduced pressure, to give the captioned compound (0.96 g, 27%) as an amorphous solid product.

Example 130

Production of $N^\alpha$-[3-(3-Cyanophenyl)acryloyl)-1-Methyl-L-Tryptophan [Compound 34]

The same procedures as in Example 121 were carried out from 1-methyl-L-tryptophan (2.0 g), sodium hydrogencarbonate (0.8 g), the compound obtained in Example 117 (2.5 g), water (60 mL), and dioxane (140 mL), to give the captioned compound (3.1 g, 90%) as crystals.

Example 131

Production of $N^\alpha$-[3-(4-Cyanophenyl)acryloyl)-1-Methyl-L-Tryptophan [Compound 36]

The same procedures as in Example 129 were carried out from 1-methyl-L-tryptophan (2.1 g), sodium hydrogencarbonate (0.8 g), the compound obtained in Example 118 (2.5 g), water (60 mL), and dioxane (140 mL), to give the captioned compound (1.8 g, 53%) as an amorphous solid product.

Example 132

Production of $N^\alpha$-[2-Cyano-3-(2-Fluorophenyl)acryloyl)-1-Methyl-L-Tryptophan [Compound 37]

To water (60 mL)-dioxane (60 mL) suspension of 1-methyl-L-tryptophan (2.1 g) was added sodium hydrogencarbonate (0.8 g) at 0° C., and the mixture was stirred for 30 minutes at room temperature. Dioxane (80 mL) solution of the compound obtained in Example 120 (2.6 g, 9.2 mmol) was added dropwise to the reaction mixture at 0° C., and the mixture was stirred for 21 hours at room temperature. The reaction mixture was concentrated to a ⅓ volume under a reduced pressure, water was added thereto, and the mixture was washed with diethyl ether. The aqueous layer was made acidic with a 10% aqueous citric acid solution, and thereafter extracted with ethyl acetate. The organic layer was washed with saturated sodium chloride solution, and thereafter dried over anhydrous sodium sulfate. The residue obtained by distilling off the solvent under a reduced pressure was purified with silica gel chromatography (BW-127ZH, chloroform: methanol=50:1), to give the captioned compound (0.6 g, 17%) as an amorphous solid product.

Example 133

Production of N-[3-(3-Cyanophenyl)acryloyl]-$O^4$-Methyl-L-Tyrosine [Compound 54]

The same procedures as in Example 129 were carried out from $O^4$-methyl-L-tyrosine (2.0 g), sodium hydrogencarbonate (0.9 g), the compound obtained in Example 117 (2.8 g), water (60 mL), and dioxane (160 mL), to give the captioned compound (1.8 g, 50%) as an amorphous solid product.

Example 134

Production of N-[3-(4-Cyanophenyl)acryloyl]-$O^4$-Methyl-L-Tyrosine [Compound 56]

The same procedures as in Example 121 were carried out from $O^4$-methyl-L-tyrosine (2.0 g), sodium hydrogencarbonate (0.9 g), the compound obtained in Example 118 (2.8 g), water (60 mL), and dioxane (160 mL), to give the captioned compound (1.6 g, 43%) as crystals.

Example 135

Production of $N^\alpha$-[3-(2-Fluorophenyl)acryloyl]-L-Glutamine [Compound 65]

The same procedures as in Example 129 were carried out from L-glutamine (2.0 g), 2,5-dioxopyrrolidin-1-yl 3-(2-fluorophenyl)acrylate (3.6 g), sodium hydrogencarbonate (1.2 g), water (60 mL), and dioxane (160 mL), to give the captioned compound (2.3 g, 58%) as crystals.

Example 136

Production of N-[3-(2-Fluorophenyl)acryloyl]-L-Tyrosine [Compound 62]

The same procedures as in Example 132 were carried out from L-tyrosine (3.0 g), pyrrolidin-1-yl 3-(2-fluorophenyl)acrylate (4.6 g), sodium hydrogencarbonate (1.5 g), water (80 mL), and dioxane (80 mL), to give the captioned compound (2.2 g, 41%) as crystals.

Example 137

Production of N-tert-Butoxycarbonyl-1-Ethyl-L-Tryptophan

Sodium hydroxide (4.6 g) was finely divided in an argon atmosphere, and thereafter methylene chloride (160 mL), N-tert-butoxycarbonyl-L-tryptophan (10.0 g), iodoethane (13.2 mL), and tetra-n-butylammonium hydrogensulfate (1.1 g) was added thereto, and the mixture was stirred for 64 hours at room temperature. The reaction mixture was washed with a 10% aqueous citric acid solution and saturated sodium chloride solution, and thereafter the organic layer was dried over anhydrous sodium sulfate. The residue obtained by distilling off the solvent under a reduced pressure was purified with silica gel column chromatography (chloroform:methanol=200:1), to give the captioned compound (5.7 g, 52%) as an oily product.

Example 138

Production of N-tert-Butoxycarbonyl-1-i-Propyl-L-Tryptophan

The same procedures as in Example 137 were carried out from sodium hydroxide (2.8 g), methylene chloride (100 mL), N-tert-butoxycarbonyl-L-tryptophan (6.0 g), 2-iodopropane (9.8 mL), and tetra-n-butylammonium hydrogensulfate (0.7 g), to give the captioned compound (1.6 g, 23%) as an oily product.

Example 139

Production of N-tert-Butoxycarbonyl-1-n-Butyl-L-Tryptophan

The same procedures as in Example 137 were carried out from sodium hydroxide (4.6 g), methylene chloride (160 mL), N-tert-butoxycarbonyl-L-tryptophan (10.0 g), 1-iodobutane (19 mL), and tetra-n-butylammonium hydrogensulfate (1.1 g), to give the captioned compound (6.2 g, 52%) as an oily product.

Example 140

Production of Methyl N-tert-Butoxycarbonyl-1-Ethyl-L-Tryptophanate

To DMF (80 mL) solution of the compound obtained in Example 137 (5,7 g) was added potassium carbonate (3.6 g) and iodomethane (1.6 mL) at 0° C., and the mixture was stirred for 17 hours at room temperature. The reaction mixture was poured into ice water, and extracted with ethyl acetate. The organic layer was dried over anhydrous sodium sulfate, and thereafter the residue obtained by distilling off the solvent under a reduced pressure was purified with silica gel column chromatography (n-hexane:ethyl acetate=5:1), to give the captioned compound (4.8 g, 81%) as an oily product.

Example 141

Production of Methyl N-tert-Butoxycarbonyl-14-Propyl-L-Tryptophanate

The same procedures as in Example 140 were carried out from the compound obtained in Example 138 (1.6 g), potassium carbonate (0.94 g), iodomethane (0.42 mL), and DMF (40 mL), to give the captioned compound (1.4 g, 86%) as an oily product.

Example 142

Production of Methyl N-tert-Butoxycarbonyl-1-n-Butyl-L-Tryptophanate

The same procedures as in Example 140 were carried out from the compound obtained in Example 139 (6.2 g), potassium carbonate (3.6 g), iodomethane (1.6 mL), and DMF (100 mL), to give the captioned compound (4.2 g, 65%) as an oily product.

Example 143

Production of Methyl 1-Ethyl-L-Tryptophanate Hydrochloride

To methylene chloride (175 mL) solution of the compound obtained in Example 140 (4.8 g) was added dropwise 4 mol/L of hydrogen chloride-dioxane solution (17.5 mL) at room temperature, and the mixture was allowed to stir for 17 hours. The crystals precipitated were filtered, and washed with diethyl ether, to give the captioned compound (2.9 g, 74%).

Example 144

Production of Methyl 1-i-Propyl-L-Tryptophanate Hydrochloride

The same procedures as in Example 143 were carried out from the compound obtained in Example 141 (1.4 g), 4 mol/L of hydrogen chloride-dioxane solution (4.8 mL), and methylene chloride (50 mL), to give the captioned compound (0.75 g, 66%) as crystals.

Example 145

Production of Methyl 1-n-Butyl-L-Tryptophanate Hydrochloride

The same procedures as in Example 143 were carried out from the compound obtained in Example 142 (4.2 g), 4 mol/L of hydrogen chloride-dioxane solution (14.0 mL), and methylene chloride (140 mL), to give the captioned compound (2.2 g, 63%) as crystals.

Example 146

Production of Methyl 1-Ethyl-N-[3-(2-Fluorophenyl) acryloyl]-L-Tryptophanate

Triethylamine (1.5 mL), 2-fluorocinnamic acid (1.8 g) and WSC.HCl (2.1 g) were at 0° C. added to methylene chloride (70 mL) suspension of the compound obtained in Example 143 (2.8 g). The mixture was stirred for 4 hours at room temperature. The reaction mixture was washed with water, and thereafter the organic layer was dried over anhydrous sodium sulfate. The residue obtained by distilling off the solvent under a reduced pressure was purified with silica gel column chromatography (chloroform), to give the captioned compound (2.7 g, 70%) as crystals.

Example 147

Production of Methyl N-[3-(2-Fluorophenyl)acryloyl]-1-i-Propyl-L-Tryptophanate

The same procedures as in Example 146 were carried out from the compound obtained in Example 144 (0.7 g), triethylamine (0.4 mL), 2-fluorocinnamic acid (0.44 g), WSC.HCl (0.50 g), and methylene chloride (20 mL), to give the captioned compound (0.9 g, 98%) as an oily product.

Example 148

Production of Methyl 1-n-Butyl-N-[3-(2-Fluorophenyl)acryloyl]-L-Tryptophanate

The same procedures as in Example 146 were carried out from the compound obtained in Example 145 (2.0 g), triethylamine (1.0 mL), 2-fluorocinnamic acid (1.2 g), WSC.HCl (1.4 g), and methylene chloride (60 mL), to give the captioned compound (2.1 g, 77%) as an oily product.

Example 149

Production of 1-Ethyl-$N^\alpha$-[3-(2-Fluorophenyl)acryloyl]-L-Tryptophan [Compound 69]

One mol/L of an aqueous sodium hydroxide solution (9.9 mL) was added dropwise to methanol (100 mL) solution of the compound obtained in Example 146 (2.6 g) at room temperature. The mixture was allowed to stir for 23 hours. The reaction mixture was concentrated to a ⅓ volume, added with water, and made acidic with dilute hydrochloric acid. The crystals precipitated were filtered, and washed with water, to give the captioned compound (2.3 g, 93%).

Example 150

Production of $N^\alpha$-[3-(2-Fluorophenyl)acryloyl]-1-i-Propyl-L-Tryptophan [Compound 70]

The same procedures as in Example 149 were carried out from the compound obtained in Example 147 (0.98 g), 1 mol/L of an aqueous sodium hydroxide solution (3.6 mL), and methanol (40 mL), to give the captioned compound (0.67 g, 71%) as crystals.

Example 151

Production of 1-n-Butyl-$N^\alpha$-[3-(2-Fluorophenyl) acryloyl]-L-Tryptophan [Compound 71]

The same procedures as in Example 149 were carried out from the compound obtained in Example 148 (2.1 g), 1 mol/L of an aqueous sodium hydroxide solution (7.5 mL), and methanol (75 mL), to give the captioned compound (1.8 g, 87%) as crystals.

Example 152

Production of Benzyl 1-Benzyl-N-tert-Butoxycarbonyl-L-Tryptophanate

The same procedures as in Example 137 were carried out from sodium hydroxide (4.6 g), methylene chloride (160 mL), N-tert-butoxycarbonyl-L-tryptophan (10.0 g), benzyl bromide (20 mL), and tetra-n-butylammonium hydrogensulfate (1.1 g), to give the captioned compound (12.2 g, 77%) as an oily product.

Example 153

Production of Benzyl 1-Benzyl-L-Tryptophanate Hydrochloride

The same procedures as in Example 143 were carried out from the compound obtained in Example 152 (12.2 g), 4 mol/L of hydrogen chloride-dioxane solution (31 mL), and methylene chloride (300 mL), to give the captioned compound (8.6 g, 81%) as crystals.

Example 154

Production of Benzyl 1-Benzyl-N43-(2-Fluorophenyl)acryloyl]-L-Tryptophanate The same procedures as in Example 146 were carried out from the compound obtained in Example 153 (1.0 g), triethylamine (0.4 mL), 2-fluorocinnamic acid (0.43 g), WSC.HCl (0.50 g) and methylene chloride (50 mL), to give the captioned compound (0.97 g, 77%) as an oily product.

Example 155

Production of 1-Benzyl-N$^\alpha$-[3-(2-Fluorophenyl)acryloyl]-L-Tryptophan [Compound 72]

The same procedures as in Example 149 were carried out from the compound obtained in Example 154 (0.97 g), 1 mol/L of an aqueous sodium hydroxide solution (2.7 mL), and methanol (27 mL), to give the captioned compound (0.57 g, 71%) as crystals.

Example 156

Production of Methyl N-[3-(2-Methylphenyl)acryloyl]-L-Tryptophanate

The same procedures as in Example 146 were carried out from methyl L-tryptophanate hydrochloride (3.0 g), triethylamine (2.0 mL), 2-methylcinnamic acid (2.3 g), WSC.HCl (2.7 g), and methylene chloride (80 mL), to give the captioned compound (4.2 g, 98%) as an oily product.

Example 157

Production of Methyl N-[3-(3-Methylphenyl)acryloyl]-L-Tryptophanate

The same procedures as in Example 146 were carried out from methyl L-tryptophanate hydrochloride (3.0 g), triethylamine (2.0 mL), 3-methylcinnamic acid (2.3 g), WSC.HCl (2.7 g), and methylene chloride (80 mL), to give the captioned compound (4.2 g, 98%) as an oily product.

Example 158

Production of Methyl N-[3-(4-Methylphenyl)acryloyl]-L-Tryptophanate

The same procedures as in Example 146 were carried out from methyl L-tryptophanate hydrochloride (3.0 g), triethylamine (2.0 mL), 4-methylcinnamic acid (2.3 g), WSC.HCl (2.7 g), and methylene chloride (80 mL), to give the captioned compound (4.3 g, 99%) as an oily product.

Example 159

Production of Methyl N43-(4-n-Butylphenyl)acryloyl]-L-Tryptophanate

The same procedures as in Example 146 were carried out from methyl L-tryptophanate hydrochloride (3.0 g), triethylamine (2.0 mL), 4-n-butylcinnamic acid (2.9 g), WSC.HCl (2.7 g), and methylene chloride (80 mL), to give the captioned compound (4.8 g, 99%) as an oily product.

Example 160

Production of Methyl N-[3-(4-i-Propylphenyl)acryloyl]-L-Tryptophanate

The same procedures as in Example 146 were carried out from methyl L-tryptophanate hydrochloride (3.0 g), triethylamine (2.0 mL), 4-i-propylcinnamic acid (2.7 g), WSC.HCl (2.7 g), and methylene chloride (80 mL), to give the captioned compound (4.5 g, 98%) as an oily product.

Example 161

Production of Methyl N-Crotonoyl-L-Tryptophanate

The same procedures as in Example 146 were carried out from methyl L-tryptophanate hydrochloride (4.0 g), triethylamine (2.6 mL), crotonic acid (1.6 g), WSC.HCl (3.6 g), and methylene chloride (110 mL), to give the captioned compound (4.4 g, 98%) as an oily product.

Example 162

Production of Methyl N-3-Methylcrotonoyl-L-Tryptophanate

The same procedures as in Example 146 were carried out from methyl L-tryptophanate hydrochloride (3.0 g), triethylamine (2.0 mL), 3-methylcrotonic acid (1.4 g), WSC.HCl (2.7 g), and methylene chloride (80 mL), to give the captioned compound (2.7 g, 77%) as crystals.

Example 163

Production of Methyl N-Tigloyl-L-Tryptophanate

The same procedures as in Example 146 were carried out from methyl L-tryptophanate hydrochloride (3.0 g), triethylamine (2.0 mL), tiglic acid (1.4 g), WSC.HCl (2.7 g), and methylene chloride (80 mL), to give the captioned compound (3.5 g, 99%) as an oily product.

Example 164

Production of Methyl
N-trans-2-Hexenoyl-L-Tryptophanate

The same procedures as in Example 146 were carried out from methyl L-tryptophanate hydrochloride (3.0 g), triethylamine (2.0 mL), trans-2-hexenoic acid (1.6 g), WSC.HCl (2.7 g), and methylene chloride (80 mL), to give the captioned compound (3.7 g, 99%) as an oily product.

Example 165

Production of Methyl
N-(2-Methyl-3-Phenylacryloyl)-L-Tryptophanate

The same procedures as in Example 146 were carried out from methyl L-tryptophanate hydrochloride (3.0 g), triethylamine (2.0 mL), α-methylcinnamic acid (2.3 g), WSC.HCl (2.7 g), and methylene chloride (80 mL), to give the captioned compound (4.0 g, 94%) as an oily product.

Example 166

Production of
N-[3-(2-Methylphenyl)acryloyl]-L-Tryptophan
[Compound 73]

The same procedures as in Example 149 were carried out from the compound obtained in Example 156 (4.2 g), 1 mol/L of an aqueous sodium hydroxide solution (17 mL), and methanol (170 mL), to give the captioned compound (3.6 g, 88%) as crystals.

Example 167

Production of
N-[3-(3-Methylphenyl)acryloyl]-L-Tryptophan
[Compound 74]

The same procedures as in Example 149 were carried out from the compound obtained in Example 157 (4.2 g), 1 mol/L of an aqueous sodium hydroxide solution (17 mL), and methanol (170 mL), to give the captioned compound (3.7 g, 92%) as crystals.

Example 168

Production of
N-[3-(4-Methylphenyl)acryloyl]-L-Tryptophan
[Compound 75]

The same procedures as in Example 149 were carried out from the compound obtained in Example 158 (4.3 g), 1 mol/L of an aqueous sodium hydroxide solution (18 mL), and methanol (180 mL), to give the captioned compound (3.7 g, 89%) as crystals.

Example 169

Production of
N-[3-(4-n-Butylphenyl)acryloyl]-L-Tryptophan
[Compound 76]

The same procedures as in Example 149 were carried out from the compound obtained in Example 159 (4.8 g), 1 mol/L of an aqueous sodium hydroxide solution (18 mL), and methanol (180 mL), to give the captioned compound (4.0 g, 87%) as crystals.

Example 170

Production of
N-[3-(4-i-Propylphenyl)acryloyl]-L-Tryptophan
[Compound 77]

The same procedures as in Example 149 were carried out from the compound obtained in Example 160 (4.5 g), 1 mol/L of an aqueous sodium hydroxide solution (17 mL), and methanol (170 mL), to give the captioned compound (3.8 g, 87%) as crystals.

Example 171

Production of N-Crotonoyl-L-Tryptophan
[Compound 78]

To methanol (230 mL) solution of the compound obtained in Example 161 (4.4 g) was added 1 mol/L of an aqueous sodium hydroxide solution (23 mL), and the mixture was allowed to stir for 20 hours. Water was added to the residue obtained by distilling off the solvent under a reduced pressure, and the mixture was made acidic with a 10% aqueous citric acid solution. The reaction mixture was extracted with ethyl acetate, the organic layer was washed with saturated sodium chloride solution, and thereafter dried over anhydrous sodium sulfate. The solvent was distilled off under a reduced pressure, to give the captioned compound (3.0 g, 71%) as an amorphous solid product.

Example 172

Production of N-3-Methylcrotonoyl-L-Tryptophan
[Compound 79]

The same procedures as in Example 171 were carried out from the compound obtained in Example 162 (2.5 g), 1 mol/L of an aqueous sodium hydroxide solution (13 mL), and methanol (130 mL), to give the captioned compound (1.9 g, 78%) as an amorphous solid product.

Example 173

Production of N-Tigloyl-L-Tryptophan [Compound 80]

The same procedures as in Example 171 were carried out from the compound obtained in Example 163 (3.5 g), 1 mol/L of an aqueous sodium hydroxide solution (18 mL), and methanol (180 mL), to give the captioned compound (2.3 g, 70%) as an amorphous solid product.

Example 174

Production of N-trans-2-Hexenoyl-L-Tryptophan
[Compound 81]

The same procedures as in Example 171 were carried out from the compound obtained in Example 164 (3.7 g), 1 mol/L of an aqueous sodium hydroxide solution (18 mL), and methanol (180 mL), to give the captioned compound (2.1 g, 58%) as an amorphous solid product.

Example 175

Production of
N-(2-Methyl-3-Phenylacryloyl)-L-Tryptophan
[Compound 82]

The same procedures as in Example 149 were carried out from the compound obtained in Example 165 (4.0 g), 1 mol/L of an aqueous sodium hydroxide solution (17 mL), and methanol (170 mL), to give the captioned compound (3.4 g, 89%) as crystals.

The data of the properties for the compound of the present invention produced and obtained as above are shown in Table 1 through 10.

TABLE 1

| Compound | Melting Point (° C.) | $^1$H-NMR Spectrum (δ, DMSO-$d_6$) |
|---|---|---|
| Compound 1 | 150-151 | 3.04 (dd, J = 8.6, 14.7 Hz, 1H), 3.21 (dd, J = 5.0, 14.7 Hz, 1H), 4.52-4.56 (m, 1H), 5.56 (dd, J = 2.0, 10.2 Hz, 1H), 6.05 (dd, J = 2.0, 17.0 Hz, 1H), 6.30 (dd, J = 10.2, 17.0 Hz, 1H), 6.95-6.98 (m, 1H), 7.03-7.06 (m, 1H), 7.11 (s, 1H), 7.32 (d, J = 8.0 Hz, 1H), 7.53 (d, J = 8.0 Hz, 1H), 8.31 (d, J = 7.9 Hz, 1H), 10.80 (s, 1H) |
| Compound 2 | 172-173 | 3.05 (dd, J = 6.9, 14.5 Hz, 1H), 3.30 (dd, J = 4.5, 14.5 Hz, 1H), 4.34-4.38 (m, 1H), 6.71-6.74 (m, 2H), 6.88-6.90 (m, 1H), 6.94-6.98 (m, 2H), 7.09-7.10 (m, 2H), 7.27 (d, J = 8.0 Hz, 1H), 7.40 (d, J = 7.2 Hz, 1H), 7.52 (d, J = 8.0 Hz, 1H), 7.61-7.64 (m, 2H), 10.77 (s, 1H) |
| Compound 3 | 104-105 | 3.08 (dd, J = 8.9, 14.7 Hz, 1H), 3.24 (dd, J = 5.0, 14.7 Hz, 1H), 4.61-4.65 (m, 1H), 6.84 (d, J = 16.0 Hz, 1H), 6.98-7.00 (m, 1H), 7.04-7.06 (m, 1H), 7.16 (d, J = 1.9 Hz, 1H), 7.26-7.34 (m, 3H), 7.45-7.48 (m, 2H), 7.56 (d, J = 7.9 Hz, 1H), 7.63-7.65 (m, 1H), 8.52 (d, J = 7.9 Hz, 1H), 10.85 (s, 1H), 12.80-13.30 (br, 1H) |
| Compound 4 | — | 3.07 (dd, J = 6.7, 14.5 Hz, 1H), 3.31 (dd, J = 4.2, 14.5 Hz, 1H), 4.36-4.37 (m, 1H), 6.87-6.90 (m, 2H), 6.97-7.00 (m, 1H), 7.10 (s, 1H), 7.16-7.17 (m, 1H), 7.27-7.42 (m, 5H), 7.52 (d, J = 7.8 Hz, 1H), 7.83 (d, J = 7.0 Hz, 1H), 10.80 (s, 1H) |
| Compound 5 | 140-141 | 3.06 (dd, J = 6.5, 14.6 Hz, 1H), 3.30 (dd, J = 4.7, 14.6 Hz, 1H), 4.31-4.34 (m, 1H), 6.78 (d, J = 15.7 Hz, 1H), 6.88 (dd, J = 7.3, 7.5 Hz, 1H), 6.98 (dd, J = 7.6, 7.5 Hz, 1H), 7.08-7.09 (m, 1H), 7.19-7.22 (m, 2H), 7.27 (d, J = 8.0 Hz, 1H), 7.33 (d, J = 15.7 Hz, 1H), 7.51 (d, J = 8.0 Hz, 1H), 7.59-7.61 (m, 2H), 7.71 (d, J = 7.5 Hz, 1H), 10.77 (s, 1H) |
| Compound 6 | 163-164 | 3.04 (dd, J = 7.0, 14.6 Hz, 1H), 3.30 (dd, J = 4.6, 14.6 Hz, 1H), 4.36-4.38 (m, 1H), 6.72 (d, J = 15.7 Hz, 1H), 6.77-8-6.78 (m, 1H), 6.78-6.92 (m, 2H), 6.98-7.00 (m, 2H), 7.09-7.14 (m, 2H), 7.22-7.28 (m, 2H), 7.53 (d, J = 7.9 Hz, 1H), 7.78 (s, 1H), 10.77 (s, 1H) |
| Compound 7 | 158-159 | 3.05 (dd, J = 6.7, 14.5 Hz, 1H), 3.27-3.31 (m, 1H), 4.36-4.38 (m, 1H), 6.54 (d, J = 15.7 Hz, 1H), 6.79 (d, J = 8.2 Hz, 2H), 6.88-6.90 (m, 1H), 6.97-7.00 (m, 1H), 7.09 (s, 1H), 7.22-7.28 (m, 2H), 7.34 (d, J = 8.2 Hz, 2H), 7.52 (d, J = 7.7 Hz, 1H), 7.60 (d, J = 6.0 Hz, 1H), 10.78 (s, 1H) |
| Compound 8 | 165-166 | 3.05 (dd, J = 6.3, 14.5 Hz, 1H), 3.29 (dd, J = 4.7, 14.5 Hz, 1H), 4.27-4.30 (m, 1H), 6.82 (d, J = 15.7 Hz, 1H), 6.87 (dd, J = 7.3, 7.5 Hz, 1H), 6.98 (dd, J = 7.5, 7.8 Hz, 1H), 7.08 (s, 1H), 7.27 (d, J = 8.0 Hz, 1H), 7.31-7.39 (m, 4H), 7.50-7.55 (m, 3H), 7.67 (d, J = 7.5 Hz, 1H), 10.73 (s, 1H) |

TABLE 2

| Compound No. | Melting Point (° C.) | $^1$H-NMR Spectrum (δ, DMSO-$d_6$) |
|---|---|---|
| Compound 9 | 124-125 | 3.09 (dd, J = 7.1, 14.5 Hz, 1H), 3.32 (dd, J = 4.6, 14.5 Hz, 1H), 4.41-4.45 (m, 1H), 6.90-6.92 (m, 1H), 6.98-7.01 (m, 1H), 7.07-7.12 (m, 2H), 7.29 (d, J = 8.1 Hz, 1H), 7.52-7.60 (m, 3H), 7.71-7.72 (m, 1H), 7.84-7.87 (m, 2H), 8.15 (d, J = 7.4 Hz, 1H), 10.79 (s, 1H) |
| Compound 10 | 114-115 | 3.09 (dd, J = 8.1, 14.6 Hz, 1H), 3.27 (dd, J = 5.0, 14.6 Hz, 1H), 4.55-4.59 (m, 1H), 6.86 (d, J = 15.5 Hz, 1H), 6.95-6.97 (m, 1H), 7.03-7.04 (m, 1H), 7.14 (d, J = 1.8 Hz, 1H), 7.32 (d, J = 8.0 Hz, 1H), 7.54-7.58 (m, 2H), 7.66-7.82 (m, 4H), 8.42 (d, J = 7.5 Hz, 1H), 10.82 (s, 1H) |
| Compound 11 | 145-146 | 3.04 (dd, J = 6.6, 14.6 Hz, 1H), 3.27 (dd, J = 4.7, 14.6 Hz, 1H), 3.84 (s, 3H), 4.28-4.29 (m, 1H), 6.76 (d, J = 15.9 Hz, 1H), 6.86-6.89 (m, 1H) 6.93-7.00 (m, 2H) 7.04 (d, J = 8.2 Hz, 1H), 7.06-7.07 (m, 1H), 7.27 (d, J = 8.2 Hz, 1H), 7.30-7.34 (m, 1H), 7.50-7.53 (m, 2H), 7.60 (d, J = 15.9 Hz, 1H), 7.64 (d, J = 7.4 Hz, 1H), 10.71 (s, 1H) |
| Compound 12 | 109-110 | 3.09 (dd, J = 8.7, 14.7 Hz, 1H), 3.25 (dd, J = 5.0, 14.7 Hz, 1H), 4.61-4.66 (m, 1H), 6.81 (d, J = 15.8 Hz, 1H), 6.98-6.99 (m, 1H), 7.05-7.06 (m, 1H), 7.16 (s, 1H), 7.33 (d, J = 8.1 Hz, 1H), 7.40-7.41 (m, 2H), 7.51-7.57 (m, 2H), 7.68-7.71 (m, 2H), 8.52 (d, J = 7.9 Hz, 1H), 10.87 (s, 1H), 12.80-13.30 (br, 1H) |

TABLE 2-continued

| Compound No. | Melting Point (° C.) | ¹H-NMR Spectrum (δ, DMSO-$d_6$) |
|---|---|---|
| Compound 13 | — | 3.02 (dd, J = 7.9, 14.6 Hz, 1H), 3.29 (dd, J = 4.1, 14.6 Hz, 1H), 4.43-4.44 (m, 1H), 6.91-7.02 (m, 3H), 7.12 (s, 1H), 7.15-7.19 (m, 2H), 7.29 (d, J = 8.0 Hz, 1H), 7.37 (d, J = 16.1 Hz, 1H), 7.43-7.44 (m, 1H), 7.54 (d, J = 7.8 Hz, 1H), 7.72 (d, J = 7.8 Hz, 1H), 10.78 (s, 1H) |
| Compound 14 | — | 3.05 (dd, J = 6.8, 14.5 Hz, 1H), 3.30 (dd, J = 4.5, 14.5 Hz, 1H), 4.34-4.35 (m, 1H), 6.85-6.89 (m, 2H), 6.88-6.89 (m, 1H), 7.09-7.11 (m, 2H), 7.26-7.29 (m, 2H), 7.38 (d, J = 15.9 Hz, 1H), 7.51 (d, J = 7.9 Hz, 1H), 7.70-7.71 (m, 1H), 7.87 (s, 1H), 10.79 (s, 1H) |
| Compound 15 | 106-107 | 3.09 (dd, J = 8.9, 14.7 Hz, 1H), 3.25 (dd, J = 4.9, 14.7 Hz, 1H), 4.61-4.66 (m, 1H), 6.87 (d, J = 16.0 Hz, 1H), 6.97-7.06 (m, 1H), 7.05-7.06 (m, 1H), 7.16 (d, J = 2.1 Hz, 1H), 7.28-7.35 (m, 3H), 7.41 (d, J = 16.0 Hz, 1H), 7.49-7.50 (m, 1H), 7.55 (d, J = 7.9 Hz, 1H), 8.53 (d, J = 7.8 Hz, 1H), 10.86 (s, 1H), 12.80-13.30 (br, 1H) |
| Compound 16 | 119-120 | 3.11 (dd, J = 8.1, 14.8 Hz, 1H), 3.28 (dd, J = 4.9, 14.8 Hz, 1H), 4.60-4.64 (m, 1H), 6.94-6.98 (m, 1H), 7.03-7.09 (m, 2H), 7.12 (s, 1H), 7.32 (d, J = 8.1 Hz, 1H), 7.54-7.60 (m, 2H), 8.08 (s, 1H), 8.27-8.30 (m, 3H), 10.86 (s, 1H) |

TABLE 3

| Compound No. | Melting Point (° C.) | ¹H-NMR Spectrum (δ, DMSO-$d_6$) |
|---|---|---|
| Compound 17 | 109-110 | 3.10 (dd, J = 8.5, 14.7 Hz, 1H), 3.26 (dd, J = 4.8, 14.7 Hz, 1H), 4.62-4.63 (m, 1H), 6.87 (d, J = 15.9 Hz, 1H), 6.97-6.99 (m, 1H), 7.04-7.06 (m, 1H), 7.16 (s, 1H), 7.33 (d, J = 8.0 Hz, 1H), 7.43 (d, J = 15.9 Hz, 1H), 7.56 (d, J = 7.9 Hz, 1H), 7.61-7.63 (m, 1H), 7.82 (d, J = 7.8 Hz, 1H), 7.89 (d, J = 7.9 Hz, 1H), 8.02 (s, 1H), 8.38 (d, J = 7.8 Hz, 1H), 10.86 (s, 1H). |
| Compound 18 | 105-106 | 3.07 (dd, J = 8.7, 14.6 Hz, 1H), 3.23 (dd, J = 5.2, 14.6 Hz, 1H), 4.60-4.65 (m, 1H), 6.65 (d, J = 15.8 Hz, 1H), 7.00-7.08 (m, 6H), 7.15-7.19 (m, 2H), 7.32-7.42 (m, 4H), 7.55-7.57 (m, 3H), 8.35 (d, J = 8.0 Hz, 1H), 10.85 (s, 1H), 12.71 (s, 1H) |
| Compound 19 | 110-111 | 3.10 (dd, J = 8.4, 14.6 Hz, 1H), 3.27 (dd, J = 4.6, 14.6 Hz, 1H), 4.61-4.65 (m, 1H), 6.89-6.98 (m, 2H), 7.04-7.07 (m, 1H), 7.15 (s, 1H), 7.32 (d, J = 8.0 Hz, 1H), 7.45 (d, J = 15.8 Hz, 1H), 7.56 (d, J = 7.8 Hz, 1H), 7.73 (d, J = 8.0 Hz, 2H), 7.86 (d, J = 8.0 Hz, 2H), 8.44 (d, J = 7.7 Hz, 1H), 10.84 (s, 1H). |
| Compound 20 | 224-225 | 3.25-3.33 (m, 2H), 4.69-4.73 (m, 1H), 6.97-6.98 (m, 1H), 7.04-7.05 (m, 1H) 7.20 (s, 1H), 7.31-7.35 (m, 2H), 7.45-7.48 (m, 1H), 7.57-7.60 (m, 2H), 7.65 (d, J = 8.4 Hz, 1H), 7.77 (d, J = 7.8 Hz, 1H), 8.76 (d, J = 7.9 Hz, 1H), 10.82 (s, 1H), 12.87 (s, 1H) |
| Compound 21 | 130-131 | 3.29-3.25 (m, 2H), 4.77-4.80 (m, 1H), 6.93-6.95 (m, 1H), 7.02-7.06 (m, 1H), 7.17 (d, J = 2.1 Hz, 1H), 7.33 (d, J = 8.1 Hz, 1H), 7.43-7.47 (m, 1H), 7.50-7.53 (m, 2H), 7.74-7.76 (m, 1H), 8.01 (d, J = 7.9 Hz, 1H), 8.93 (s, 1H), 9.10 (d, J = 7.3 Hz, 1H), 10.93 (s, 1H), 12.80-13.30 (br, 1H) |
| Compound 22 | 124-125 | 3.21-3.33 (m, 2H), 4.57-4.61 (m, 1H), 6.98-7.00 (m, 1H), 7.05-7.08 (m, 1H), 7.20 (s, 1H), 7.34 (d, J = 8.0 Hz, 1H), 7.40-7.44 (m, 2H), 7.58 (d, J = 7.8 Hz, 1H), 7.65-7.67 (m, 1H), 8.06-8.09 (m, 1H), 8.20 (s, 1H), 8.74 (d, J = 7.6 Hz, 1H), 10.88 (s, 1H), 12.80-13.33 (br, 1H) |
| Compound 23 | 200-201 | 2.99 (dd, J = 9.1, 14.6 Hz, 1H), 3.18 (dd, J = 4.7, 14.6 Hz, 1H), 4.64-4.68 (m, 1H), 6.84 (d, J = 16.0 Hz, 1H), 6.97-6.99 (m, 1H), 7.05-7.08 (m, 2H), 7.15 (d, J = 1.1 Hz, 1H), 7.25-7.32 (m, 3H), 4.28-4.60 (m, 2H), 7.56-7.66 (m, 3H), 8.38 (d, J = 8.2 Hz, 1H), 10.79 (s, 1H) |
| Compound 24 | 104-105 | 3.08 (dd, J = 8.8, 14.7 Hz, 1H), 3.24 (dd, J = 4.9, 14.7 Hz, 1H), 4.61-4.64 (m, 1H), 6.84 (d, J = 16.0 Hz, 1H), 6.98-7.00 (m, 1H), 7.05-7.06 (m, 1H), 7.16 (d, J = 1.4 Hz, 1H), 7.25-7.34 (m, 3H), 7.42-7.48 (m, 2H), 7.54-7.57 (m, 1H), 7.63-7.65 (m, 1H), 8.53 (d, J = 7.9 Hz, 1H), 10.85 (s, 1H), 12.74 (s, 1H) |

TABLE 4

| Compound No. | Melting Point (° C.) | ¹H-NMR Spectrum (δ, DMSO-$d_6$) |
|---|---|---|
| Compound 25 | 124-125 | 3.23 (dd, J = 9.1, 14.7 Hz, 1H), 3.32 (dd, J = 4.7, 14.7 Hz, 1H), 4.58-4.62 (m, 1H), 6.97-7.00 (m, 1H), 7.05-7.08 (m, 1H), 7.20 (d, J = 2.1 Hz, 1H), 7.34 (d, J = 8.1 Hz, 1H), 7.56-7.60 (m, 4H), 7.90-7.91 (m, 2H), 8.10 (s, 1H), 8.59 (d, J = 7.7 Hz, 1H), 10.89 (s, 1H), 12.93 (s, 1H) |
| Compound 26 | 95-96 | 3.07 (dd, J = 8.7, 14.7 Hz, 1H), 3.21 (dd, J = 5.1, 14.7 Hz, 1H), 3.72 (s, 3H), 4.59-4.61 (m, 1H), 6.74 (d, J = 16.0 Hz, 1H), 6.81-6.82 (m, 1H), 6.87-6.89 (m, 1H), 7.01-7.03 (m, 1H), 7.17-7.19 (m, 3H), 7.36-7.41 (m, 2H), 7.57-7.63 (m, 2H), 8.34 (d, J = 7.8 Hz, 1H), 8.34 (d, J = 7.8 Hz, 1H), 12.80-13.00 (br, 1H) |
| Compound 27 | 100-101 | 3.09 (dd, J = 8.5, 14.6 Hz, 1H), 3.23 (dd, J = 5.0, 14.6 Hz, 1H), 3.72 (s, 3H), 4.60-4.63 (m, 1H), 6.84 (d, J = 15.9 Hz, 1H), 7.02-7.13 (m, 1H), 7.11-7.13 (m, 2H), 7.26-7.29 (m, 2H), 7.36-7.37 (m, 1H), 7.42-7.49 (m, 2H), 7.57 (d, J = 7.8 Hz, 1H), 7.63-7.65 (m, 1H), 8.51 (d, J = 7.7 Hz, 1H), 12.71 (s, 1H) |
| Compound 28 | 86-87 | 3.09 (dd, J = 8.4, 14.6 Hz, 1H), 3.22 (dd, J = 5.2, 14.6 Hz, 1H), 3.72 (s, 3H), 4.60-4.64 (m, 1H), 6.69 (d, J = 15.8 Hz, 1H), 7.02-7.03 (m, 1H), 7.13-7.14 (m, 2H), 7.23-7.27 (m, 2H), 7.36-7.42 (m, 2H), 7.56-7.63 (m, 3H), 8.37 (d, J = 7.8 Hz, 1H), 12.60-12.80 (br, 1H) |
| Compound 29 | 100-101 | 3.08 (dd, J = 7.7, 14.5 Hz, 1H), 3.25 (dd, J = 5.2, 14.5 Hz, 1H), 3.70 (s, 3H), 4.53-4.56 (m, 1H), 6.77 (d, J = 15.8 Hz, 1H), 6.96-6.99 (m, 1H), 7.08-7.10 (m, 2H), 7.33-7.41 (m, 5H), 7.54-7.58 (m, 3H), 8.20 (d, J = 7.6 Hz, 1H) |
| Compound 30 | — | 3.11 (dd, J = 8.3, 14.7 Hz, 1H), 3.24 (dd, J = 5.3, 14.7 Hz, 1H), 3.73 (s, 3H), 4.63-4.65 (m, 1H), 6.96-7.02 (m, 2H), 7.13-7.14 (m, 2H), 7.37 (d, J = 8.2 Hz, 1H), 7.56-7.64 (m, 3H), 7.76-7.77 (m, 1H), 7.83-7.84 (m, 1H), 7.90 (d, J = 7.7 Hz, 1H), 8.61 (d, J = 7.8 Hz, 1H), 12.80 (s, 1H) |
| Compound 31 | 99-100 | 3.07 (dd, J = 8.8, 14.6 Hz, 1H), 3.23 (dd, J = 4.8, 14.6 Hz, 1H), 3.72 (s, 3H), 4.60-4.64 (m, 1H), 6.96 (d, J = 16.1 Hz, 1H), 7.00-7.04 (m, 1H), 7.12-7.21 (m, 4H), 7.36-7.47 (m, 3H), 7.57 (d, J = 7.9 Hz, 1H), 8.70 (d, J = 7.7 Hz, 1H), 12.73 (s, 1H) |
| Compound 32 | 99-100 | 3.08 (dd, J = 8.5, 14.4 Hz, 1H), 3.22 (dd, J = 4.7, 14.4 Hz, 1H), 3.72 (s, 3H), 4.61-4.62 (m, 1H), 6.80 (d, J = 15.9 Hz, 1H), 7.00-7.03 (m, 1H), 7.13-7.18 (m, 3H), 7.32-7.44 (m, 3H), 7.57 (d, J = 7.7 Hz, 1H), 7.70 (d, J = 7.1 Hz, 1H), 8.51 (d, J = 7.4 Hz, 1H), 12.74 (s, 1H) |
| Compound 33 | 75-76 | 3.09 (dd, J = 8.5, 14.7 Hz, 1H), 3.23 (dd, J = 5.1, 14.7 Hz, 1H), 3.72 (s, 3H), 4.60-4.64 (m, 1H), 6.87 (d, J = 16.0 Hz, 1H), 7.00-7.03 (m, 1H), 7.12-7.15 (m, 2H), 7.34-7.43 (m, 4H), 7.48-7.50 (m, 1H), 7.57 (d, J = 7.9 Hz, 1H), 8.53 (d, J = 7.8 Hz, 1H), 12.60-12.80 (br, 1H) |

TABLE 5

| Compound No. | Melting Point (° C.) | ¹H-NMR Spectrum (δ, DMSO-$d_6$) |
|---|---|---|
| Compound 34 | 104-105 | 3.11 (dd, J = 8.2, 14.6 Hz, 1H), 3.25 (dd, J = 5.3, 14.6 Hz, 1H), 3.72 (s, 3H), 4.60-4.64 (m, 1H), 6.87 (d, J = 15.8 Hz, 1H), 7.00-7.02 (m, 1H), 7.11-7.13 (m, 2H), 7.36 (d, J = 8.2 Hz, 1H), 7.44 (d, J = 15.8 Hz, 1H), 7.56-7.63 (m, 2H), 7.82 (d, J = 7.6 Hz, 1H), 7.89 (d, J = 7.7 Hz, 1H), 8.02 (s, 1H), 8.38 (d, J = 7.4 Hz, 1H) |
| Compound 35 | 98-99 | 3.08 (dd, J = 8.5, 14.6 Hz, 1H), 3.22 (dd, J = 5.2, 14.6 Hz, 1H), 3.72 (s, 3H), 4.59-4.63 (m, 1H), 6.65 (d, J = 15.8 Hz, 1H), 7.00-7.19 (m, 8H), 7.36-7.44 (m, 4H), 7.56-7.58 (m, 3H), 8.35 (s, J = 4.7 Hz, 1H), 12.72 (s, 1H) |
| Compound 36 | — | 3.10 (dd, J = 8.3, 14.7 Hz, 1H), 3.24 (dd, J = 5.2, 14.7 Hz, 1H), 3.72 (s, 3H), 4.61-4.66 (m, 1H), 6.89 (d, J = 15.9 Hz, 1H), 7.00-7.03 (m, 1H), 7.11-7.14 (m, 2H), 7.37 (d, J = 8.2 Hz, 1H), 7.47 (d, J = 15.9 Hz, 1H), 7.57 (d, J = 7.8 Hz, 1H), 7.74 (d, J = 8.2 Hz, 2H), 7.87 (d, J = 8.2 Hz, 2H), 8.49 (d, J = 7.8 Hz, 1H), 12.60-12.80 (br, 1H) |

TABLE 5-continued

| Compound No. | Melting Point (° C.) | $^1$H-NMR Spectrum (δ, DMSO-$d_6$) |
|---|---|---|
| Compound 37 | — | 3.22 (dd, J = 9.1, 14.7 Hz, 1H), 3.30 (dd, J = 4.8, 14.7 Hz, 1H), 3.73 (s, 3H), 4.55-4.59 (m, 1H), 7.01-7.04 (m, 1H), 7.12-7.18 (m, 2H), 7.37-7.45 (m, 3H), 7.60 (d, J = 7.9 Hz, 1H), 7.66-7.67 (m, 1H), 8.06-8.08 (m, 1H), 8.18 (s, 1H), 8.77 (d, J = 7.7 Hz, 1H), 12.94 (s, 1H) |
| Compound 38 | 90-91 | 2.83 (dd, J = 8.5, 13.7 Hz, 1H), 3.03 (dd, J = 4.8, 13.7 Hz, 1H), 3.70 (s, 3H), 4.31-4.35 (m, 1H), 5.53 (dd, J = 2.0, 10.3 Hz, 1H), 6.02 (dd, J = 2.0, 17.0 Hz, 1H), 6.29 (dd, J = 10.3, 17.0 Hz, 1H), 6.79 (d, J = 8.5 Hz, 2H), 7.10 (d, J = 8.5 Hz, 2H), 8.07 (d, J = 7.6 Hz, 1H) |
| Compound 39 | — | 2.86 (dd, J = 9.7, 13.8 Hz, 1H), 3.05 (dd, J = 4.8, 13.8 Hz, 1H), 3.71 (s, 3H), 6.72 (d, J = 15.9 Hz, 1H), 6.81-6.85 (m, 3H), 6.90 (d, J = 8.1 Hz, 1H), 7.17-7.19 (m, 3H), 7.41 (d, J = 7.5 Hz, 1H), 7.60 (d, J = 15.9 Hz, 1H), 8.35 (d, J = 8.1 Hz, 1H), 10.05 (s, 1H), 12.60-12.80 (br, 1H) |
| Compound 40 | 191-192 | 2.87 (dd, J = 9.5, 13.9 Hz, 1H), 3.06 (dd, J = 4.8, 13.9 Hz, 1H), 3.71 (s, 1H), 4.52-4.54 (m, 1H), 6.80-6.84 (m, 3H), 7.17 (d, J = 8.6 Hz, 2H), 7.25-7.30 (m, 2H), 7.43-7.48 (m, 2H), 7.63-7.66 (m, 1H), 8.52 (d, J = 8.1 Hz, 1H), 12.77 (s, 1H) |
| Compound 41 | 189-190 | 2.88 (dd, J = 9.4, 13.8 Hz, 1H), 3.06 (dd, J = 4.5, 13.8 Hz, 1H), 3.71 (s, 3H), 4.51-4.55 (m, 1H), 6.76 (d, J = 15.9 Hz, 1H), 6.84 (d, J = 8.4 Hz, 2H), 7.16-7.23 (m, 3H), 7.38-7.47 (m, 4H), 8.40 (d, J = 8.0 Hz, 1H), 12.80 (s, 1H) |
| Compound 42 | 203-204 | 2.87 (dd, J = 9.3, 13.9 Hz, 1H), 3.06 (dd, J = 4.6, 13.9 Hz, 1H), 3.71 (s, 3H), 4.50-4.55 (m, 1H), 6.67 (d, J = 15.8 Hz, 1H), 6.84 (d, J = 8.3 Hz, 2H), 7.17 (d, J = 8.3 Hz, 2H), 7.23-7.27 (m, 2H), 7.40 (d, J = 15.8 Hz, 1H), 7.61-7.63 (m, 2H), 8.37 (d, J = 8.1 Hz, 1H) |

TABLE 6

| Compound No. | Melting Point (° C.) | $^1$H-NMR Spectrum (δ, DMSO-$d_6$) |
|---|---|---|
| Compound 43 | — | 2.85 (dd, J = 9.6, 13.8 Hz, 1H), 3.05 (dd, J = 4.8, 13.8 Hz, 1H), 3.70 (s, 3H), 4.48-4.53 (m, 1H), 6.62 (d, J = 15.8 Hz, 1H), 6.78 (d, J = 8.1 Hz, 1H), 6.84 (d, J = 8.4 Hz, 2H), 6.92 (s, 1H), 6.96 (d, J = 7.6 Hz, 1H), 7.16-7.22 (m, 3H), 7.28 (d, J = 15.8 Hz, 1H), 8.39 (d, J = 8.1 Hz, 1H), 9.58 (s, 1H), 12.70-12.90 (br, 1H) |
| Compound 44 | — | 2.86 (dd, J = 9.5, 13.8 Hz, 1H), 3.04 (dd, J = 4.7, 13.8 Hz, 1H), 3.70 (s, 3H), 4.48-4.52 (m, 1H), 6.49 (d, J = 15.8 Hz, 1H), 6.79 (d, J = 8.4 Hz, 2H), 6.84 (d, J = 8.4 Hz, 2H), 7.17 (d, J = 8.4 Hz, 2H), 7.29 (d, J = 15.8 Hz, 1H), 7.39 (d, J = 8.4 Hz, 2H), 8.25 (d, J = 8.1 Hz, 1H), 9.86 (s, 1H), 12.60-12.80 (br, 1H) |
| Compound 45 | 170-171 | 2.89 (dd, J = 8.7, 13.8 Hz, 1H), 3.10 (dd, J = 4.5, 13.8 Hz, 1H), 3.69 (s, 3H), 4.45-4.49 (m, 1H), 6.76-6.82 (m, 3H), 7.15-7.17 (m, 2H), 7.36-7.42 (m, 4H), 7.55-7.56 (m, 2H), 8.23 (d, J = 8.0 Hz, 1H) |
| Compound 46 | 229-230 | 2.89 (dd, J = 9.3, 13.8 Hz, 1H), 3.08 (dd, J = 4.7, 13.8 Hz, 1H), 3.71 (s, 3H), 4.53-4.57 (m, 1H), 6.85 (d, J = 8.4 Hz, 2H), 6.95 (d, J = 15.6 Hz, 1H), 7.18 (d, J = 8.4 Hz, 2H), 7.57-7.63 (m, 2H), 7.76-7.79 (m, 1H), 7.85 (d, J = 8.4 Hz, 1H), 8.63 (d, J = 7.9 Hz, 1H), 8.63 (d, J = 7.9 Hz, 1H), 12.80-13.00 (br, 1H) |
| Compound 47 | 79-80 | 2.89 (dd, J = 9.3, 13.9 Hz, 1H), 3.07 (dd, J = 4.9, 13.9 Hz, 1H), 3.71 (s, 3H), 4.51-4.56 (m, 1H), 6.80-6.86 (m, 3H), 7.18 (d, J = 8.4 Hz, 2H), 7.58-7.62 (m, 1H), 7.67 (d, J = 15.4 Hz, 1H), 7.73-7.84 (m, 3H), 8.57 (d, J = 8.0 Hz, 1H), 12.70-12.90 (br, 1H) |
| Compound 48 | 145-146 | 2.86 (dd, J = 9.7, 13.9 Hz, 1H), 3.04 (dd, J = 4.7, 13.9 Hz, 1H), 3.70 (s, 3H), 3.85 (s, 3H), 4.48-4.52 (m, 1H), 6.72 (d, J = 15.9 Hz, 1H), 6.84 (d, J = 8.6 Hz, 2H), 6.97-7.00 (m, 1H), 7.06-7.07 (m, 1H), 7.16 (d, J = 8.6 Hz, 1H), 7.35-7.38 (m, 1H), 7.49-7.50 (m, 1H), 7.61 (d, J = 15.9 Hz, 1H), 8.36 (d, J = 7.8 Hz, 1H) |
| Compound 49 | 189-190 | 2.88 (dd, J = 9.5, 13.9 Hz, 1H), 3.06 (dd, J = 4.7, 13.9 Hz, 1H), 3.71 (s, 3H), 4.51-4.55 (m, 1H), 6.78 (d, J = 15.7 Hz, 1H), 6.85 (d, J = 8.5 Hz, 2H), 7.17 (d, J = 8.5 Hz, 2H), 7.40-7.42 (m, 2H), 7.52-7.54 (m, 1H), 7.68-7.71 (m, 2H), 8.52 (d, J = 8.0 Hz, 1H), 12.80 (s, 1H) |

TABLE 6-continued

| Compound No. | Melting Point (° C.) | ¹H-NMR Spectrum (δ, DMSO-$d_6$) |
|---|---|---|
| Compound 50 | 84-85 | 2.86 (dd, J = 9.7, 13.9 Hz, 1H), 3.07 (dd, J = 4.7, 13.9 Hz, 1H), 3.71 (s, 3H), 4.51-4.55 (m, 1H), 6.85 (d, J = 8.4 Hz, 2H), 6.94 (d, J = 16.1 Hz, 1H), 7.17-7.22 (m, 4H), 7.41 (d, J = 16.1 Hz, 1H), 7.46-7.49 (m, 1H), 8.70 (d, J = 8.0 Hz, 1H), 12.79 (s, 1H) |
| Compound 51 | 197-198 | 2.87 (dd, J = 9.6, 13.8 Hz, 1H), 3.06 (dd, J = 4.6, 13.8 Hz, 1H), 3.71 (s, 3H), 4.50-4.55 (m, 1H), 6.78 (d, J = 16.0 Hz, 1H), 6.85 (d, J = 8.2 Hz, 2H), 7.16-7.18 (m, 3H), 7.33-7.37 (m, 1H), 7.41 (d, J = 16.0 Hz, 1H), 7.69-7.74 (m, 1H), 8.53 (d, J = 8.0 Hz, 1H), 12.60-12.80 (br, 1H) |

TABLE 7

| Compound No. | Melting Point (° C.) | ¹H-NMR Spectrum (δ, DMSO-$d_6$) |
|---|---|---|
| Compound 52 | 154-155 | 2.88 (dd, J = 9.7, 13.6 Hz, 1H), 3.07 (dd, J = 4.3, 13.6 Hz, 1H), 3.71 (s, 3H), 4.51-4.55 (m, 1H), 6.84-6.86 (m, 3H), 7.18 (d, J = 8.0 Hz, 2H), 7.29-7.42 (m, 3H), 7.51-7.52 (m, 1H), 8.54 (d, J = 8.0 Hz, 1H), 12.60-12.80 (br, 1H) |
| Compound 53 | 91-92 | 2.89 (dd, J = 9.2, 13.9 Hz, 1H), 3.08 (dd, J = 4.8, 13.9 Hz, 1H), 3.71 (s, 3H), 4.54-4.58 (m, 1H), 6.85 (d, J = 8.4 Hz, 2H), 7.05 (d, J = 15.9 Hz, 1H), 7.17 (d, J = 8.4 Hz, 2H), 7.59 (d, J = 15.9 Hz, 1H), 8.09 (s, 1H), 8.27 (s, 2H), 8.36 (d, J = 8.0 Hz, 1H), 12.85 (s, 1H) |
| Compound 54 | — | 2.91 (dd, J = 9.5, 14.0 Hz, 1H), 3.11 (dd, J = 4.9, 14.0 Hz, 1H), 3.72 (s, 3H), 4.57-4.62 (m, 1H), 6.85-6.87 (m, 3H), 7.19-7.21 (m, 2H), 7.47 (d, J = 15.9 Hz, 1H), 7.61-7.64 (m, 1H), 7.83 (d, J = 7.7 Hz, 1H), 7.91 (d, J = 8.0 Hz, 1H), 8.03-8.04 (m, 1H), 8.45 (d, J = 8.1 Hz, 1H), 12.70-12.90 (br, 1H) |
| Compound 55 | 205-206 | 2.86 (dd, J = 9.5, 13.8 Hz, 1H), 3.04 (dd, J = 4.8, 13.8 Hz, 1H), 3.70 (s, 3H), 4.49-4.53 (m, 1H), 6.62 (d, J = 15.8 Hz, 1H), 6.84 (d, J = 8.6 Hz, 2H), 7.01 (d, J = 8.7 Hz, 2H), 7.07 (d, J = 8.0 Hz, 2H), 7.15-7.19 (m, 3H), 7.37 (d, J = 15.8 Hz, 1H), 7.41-7.44 (m, 2H), 7.57 (d, J = 8.7 Hz, 2H), 8.35 (d, J = 8.1 Hz, 1H), 12.75 (s, 1H) |
| Compound 56 | 212-213 | 2.88 (dd, J = 9.3, 13.8 Hz, 1H), 3.07 (dd, J = 4.8, 13.8 Hz, 1H), 3.70 (s, 3H), 4.51-4.56 (m, 1H), 6.83-6.88 (m, 3H), 7.16 (d, J = 8.4 Hz, 2H), 7.45 (d, J = 15.9 Hz, 1H), 7.74 (d, J = 8.1 Hz, 2H), 7.87 (d, J = 8.1 Hz, 2H), 8.48 (d, J = 8.0 Hz, 1H) |
| Compound 57 | 125-126 | 3.08 (dd, J = 10.4, 13.7 Hz, 1H), 3.17 (dd, J = 3.9, 13.7 Hz, 1H), 3.69 (s, 3H), 4.61-4.66 (m, 1H), 6.83 (d, J = 8.5 Hz, 2H), 7.23 (d, J = 8.5 Hz, 2H), 7.33-7.36 (m, 1H), 7.46-7.49 (m, 1H), 7.59 (s, 1H), 7.68 (d, J = 8.4 Hz, 1H), 7.78 (d, J = 7.8 Hz, 1H), 8.88 (d, J = 8.2 Hz, 1H), 12.60-13.0 (br, 1H) |
| Compound 58 | 177-178 | 3.05 (dd, J = 6.7, 13.9 Hz, 1H), 3.13 (dd, J = 5.2, 13.9 Hz, 1H), 3.71 (s, 1H), 4.71-4.74 (m, 1H), 6.84 (d, J = 8.5 Hz, 2H), 7.12 (d, J = 8.5 Hz, 2H), 7.44-7.47 (m, 1H), 7.52 (d, J = 8.3 Hz, 1H), 7.76-7.79 (m, 1H), 8.01 (d, J = 7.6 Hz, 1H), 8.92 (s, 1H), 9.02 (d, J = 7.4 Hz, 1H), 13.00-13.30 (br, 1H) |
| Compound 59 | — | 0.88 (d, J = 6.4 Hz, 3H), 0.92 (d, J = 6.4 Hz, 3H), 1.56-1.67 (m, 3H), 4.36-4.38 (m, 1H), 6.84 (d, J = 16.0 Hz, 1H), 7.26-7.31 (m, 2H), 7.44-7.45 (m, 1H), 7.51 (d, J = 16.0 Hz, 1H), 7.65-7.68 (m, 1H), 8.50 (d, J = 7.9 Hz, 1H), 12.50-12.70 (br, 1H) |
| Compound 60 | 110-111 | 1.85-1.94 (m, 2H), 2.23-2.51 (m, 2H), 4.28-4.32 (m, 1H), 6.93 (d, J = 15.9 Hz, 1H), 7.25-7.30 (m, 2H), 7.41-7.45 (m, 1H), 7.50 (d, J = 15.9 Hz, 1H), 7.67-7.70 (m, 1H), 8.27 (d, J = 7.7 Hz, 1H) |
| Compound 61 | 116-119 | 1.41-1.43 (m, 2H), 1.56-1.78 (m, 4H), 2.75-2.78 (m, 2H), 4.29-4.33 (m, 1H), 6.91 (d, J = 16.0 Hz, 1H), 7.26-7.31 (m, 2H), 7.43-7.47 (m, 1H), 7.51 (d, J = 16.0 Hz, 1H), 7.65-7.68 (m, 1H), 8.03 (s, 3H), 8.61 (d, J = 7.7 Hz, 1H) |

TABLE 8

| Compound No. | Melting Point (° C.) | ¹H-NMR Spectrum (δ, DMSO-$d_6$) |
|---|---|---|
| Compound 62 | 124-125 | 2.81 (dd, J = 9.6, 13.8 Hz, 1H), 3.00 (d, J = 4.7, 13.8 Hz, 1H), 4.47-4.51 (m, 1H), 6.66 (d, J = 8.3 Hz, 2H), 6.81 (d, J = 16.0 Hz, 1H), 7.04 (d, J = 8.3 Hz, 2H), 7.25-7.30 (m, 2H), 7.42-7.47 (m, 2H), 7.63-7.66 (m, 1H), 8.50 (d, J = 7.9 Hz, 1H), 9.22 (s, 1H), 12.75 (s, 1H) |
| Compound 63 | 189-190 | 1.64-1.71 (m, 3H), 1.85-1.86 (m, 1H), 7.79-2.80 (m, 2H), 4.35-4.37 (m, 1H), 6.91 (d, J = 16.0 Hz, 1H), 7.27-7.32 (m, 2H), 7.43-7.46 (m, 1H), 7.52 (d, J = 16.0 Hz, 1H), 7.65-7.68 (m, 1H), 8.05 (s, 3H), 8.68 (d, J = 7.9 Hz, 1H) |
| Compound 64 | 124-125 | 1.39-1.55 (m, 2H), 1.64-1.68 (m, 1H), 1.79-1.82 (m, 1H), 3.12-3.13 (m, 2H), 4.33-4.38 (m, 1H), 6.87 (d, J = 15.9 Hz, 1H), 7.26-7.31 (m, 2H), 7.43-7.53 (m, 2H), 7.67-7.69 (m, 1H), 8.54 (d, J = 7.8, 1H) |
| Compound 65 | 169-170 | 1.80-1.83 (m, 1H), 2.02-2.04 (m, 1H), 2.15-2.19 (m, 2H), 4.29-4.33 (m, 1H), 6.79-6.85 (m, 2H), 7.26-7.31 (m, 3H), 7.43-7.45 (m, 1H), 7.51 (d, J = 16.0 Hz, 1H), 7.65-7.68 (m, 1H), 8.52 (d, J = 7.8 Hz, 1H), 12.66 (s, 1H) |
| Compound 66 | 177-178 | 3.68-3.71 (m, 1H), 3.76-3.79 (m, 1H), 4.42-4.46 (m, 1H), 5.00-5.10 (br, 1H), 6.97 (d, J = 16.0 Hz, 1H), 7.26-7.31 (m, 2H), 7.43-7.46 (m, 1H), 7.52 (d, J = 16.0 Hz, 1H), 7.65-7.68 (m, 1H), 8.43 (d, J = 8.0 Hz, 1H), 12.65-12.75 (br, 1H) |
| Compound 67 | 138-139 | 1.91-1.94 (m, 1H), 2.01-2.06 (m, 4H), 2.51-2.52 (m, 2H), 4.43-4.47 (m, 1H), 6.83 (d, J = 16.0 Hz, 1H), 7.26-7.31 (m, 2H), 7.43-7.45 (m, 1H), 7.51 (d, J = 16.0 Hz, 1H), 7.66-7.67 (m, 1H), 8.54 (d, J = 7.8 Hz, 1H), 12.60-12.80 (br, 1H) |
| Compound 68 | 109-110 | 3.08 (dd, J = 8.9, 14.5 Hz, 1H), 3.24 (dd, J = 4.8, 14.5 Hz, 1H), 4.61-4.65 (m, 1H), 6.84 (dd, J = 16.0 Hz, 1H), 6.97-6.99 (m, 1H), 7.04-7.06 (m, 1H), 7.16 (s, 1H), 7.25-7.33 (m, 3H), 7.42-7.48 (m, 2H), 7.55 (d, J = 7.9 Hz, 1H), 7.63-7.64 (m, 1H), 8.51 (d, J = 7.8 Hz, 1H), 10.85 (s, 1H), 12.56-12.66 (br, 1H) |

TABLE 9

| Compound No. | Melting Point (° C.) | ¹H-NMR Spectrum (δ, DMSO-$d_6$) |
|---|---|---|
| Compound 69 | 92-93 | 1.30 (t, J = 7.2 Hz, 3H), 3.08 (dd, J = 8.6, 14.6 Hz, 1H), 3.23 (dd, J = 5.1, 14.6 Hz, 1H), 4.13 (q, J = 7.2 Hz, 2H), 4.61-4.65 (m, 1H), 6.84 (d, J = 16.0 Hz, 1H), 7.01-7.02 (m, 1H), 7.10-7.11 (m, 1H), 7.19 (s, 1H), 7.26-7.30 (m, 2H), 7.40-7.49 (m, 3H), 7.56-7.58 (m, 1H), 7.63-7.65 (m, 1H), 8.53 (d, J = 7.9 Hz, 1H), 12.74 (s, 1H) |
| Compound 70 | 85-86 | 1.38-1.41 (m, 6H), 3.08 (dd, J = 8.8, 14.6 Hz, 1H), 3.25 (dd, J = 5.1, 14.6 Hz, 1H), 4.61-4.69 (m, 2H), 6.83 (d, J = 16.1 Hz, 1H), 7.00-7.02 (m, 1H), 7.09-7.11 (m, 1H), 7.26-7.29 (m, 3H), 7.43-7.49 (m, 3H), 7.56 (d, J = 7.9 Hz, 1H), 7.63-7.64 (m, 1H), 8.52 (d, J = 7.9 Hz, 1H), 12.75 (s, 1H) |
| Compound 71 | 71-72 | 0.79 (t, J = 7.3 Hz, 3H), 1.14-1.19 (m, 2H), 1.64-1.67 (m, 2H), 3.05-3.08 (m, 1H), 3.22-3.25 (m, 1H), 4.07-4.11 (m, 2H), 4.62-4.63 (m, 1H), 6.82 (d, J = 15.9 Hz, 1H), 7.00-7.02 (m, 1H), 7.09-7.11 (m, 1H), 7.16 (s, 1H), 7.26-7.29 (m, 2H), 7.39-7.48 (m, 3H), 7.56 (d, J = 7.9 Hz, 1H), 7.61-7.63 (m, 1H), 8.52 (d, J = 8.0 Hz, 1H), 12.76 (s, 1H) |
| Compound 72 | 83-84 | 3.08 (dd, J = 9.1, 14.6 Hz, 1H), 3.27 (dd, J = 5.0, 14.6 Hz, 1H), 4.63-4.67 (m, 1H), 5.35 (s, 2H), 6.82 (d, J = 16.0 Hz, 1H), 7.01-7.19 (m, 7H), 7.26-7.31 (m, 3H), 7.36-7.38 (m, 1H), 7.45-7.49 (m, 2H), 7.57-7.63 (m, 2H), 8.55 (d, J = 7.9 Hz, 1H), 12.77 (s, 1H) |
| Compound 73 | 236-237 | 2.35 (s, 3H), 3.08 (dd, J = 8.7, 14.7 Hz, 1H), 3.24 (dd, J = 5.1, 14.7 Hz, 1H), 4.62-4.66 (m, 1H), 6.64 (d, J = 15.7 Hz, 1H), 6.98-7.00 (m, 1H), 7.05-7.07 (m, 1H), 7.16 (d, J = 2.0 Hz, 1H), 7.23-7.25 (m, 3H), 7.33 (d, J = 8.1 Hz, 1H), 7.51 (d, J = 7.3 Hz, 1H), 7.56 (d, J = 8.1 Hz, 1H), 7.62 (d, J = 15.7 Hz, 1H), 8.42 (d, J = 7.9 Hz, 1H), 10.85 (s, 1H), 12.50-12.85 (br, 1H) |
| Compound 74 | 237-238 | 2.32 (s, 3H), 3.08 (dd, J = 8.8, 14.7 Hz, 1H), 3.24 (dd, J = 5.0 Hz, 14.7 Hz, 1H), 4.60-4.65 (m, 1H), 6.73 (d, J = 15.9 Hz, 1H), 6.98-7.00 (m, 1H), 7.05-7.06 (m, 1H), 7.16-7.20 (m, 2H), 7.29-7.37 (m, 5H), 7.56 (d, J = 7.9 Hz, 1H), 8.35 (d, J = 7.9 Hz, 1H), 10.85 (s, 1H), 12.50-12.90 (br, 1H) |

TABLE 9-continued

| Compound No. | Melting Point (° C.) | $^1$H-NMR Spectrum (δ, DMSO-$d_6$) |
|---|---|---|
| Compound 75 | 255-256 | 2.32 (s, 3H), 3.08 (dd, J = 8.9, 14.7 Hz, 1H), 3.23 (dd, J = 4.6, 14.7 Hz, 1H), 4.61-4.65 (m, 1H), 6.68 (d, J = 15.8 Hz, 1H), 6.96-6.99 (m, 1H), 7.05-7.07 (m, 1H), 7.16 (s, 1H), 7.21-7.23 (m, 2H), 7.32-7.37 (m, 2H), 7.43-7.44 (m, 2H), 7.55 (d, J = 7.9 Hz, 1H), 8.34 (d, J = 7.8 Hz, 1H), 10.85 (s, 1H), 12.71 (s, 1H) |
| Compound 76 | 214-215 | 0.89 (t, J = 7.3 Hz, 3H), 1.27-1.32 (m, 2H), 1.52-1.56 (m, 2H), 2.58 (t, J = 7.6 Hz, 2H), 3.09 (dd, J = 8.8, 14.7 Hz, 1H), 3.24 (dd, J = 4.9, 14.7 Hz, 1H), 4.61-4.64 (m, 1H), 6.70 (d, J = 15.8 Hz, 1H), 6.97-7.00 (m, 1H), 7.05-7.08 (m, 1H), 7.17 (s, 1H), 7.22 (d, J = 8.0 Hz, 2H), 7.33-7.38 (m, 2H), 7.45 (d, J = 8.0 Hz, 2H), 7.56 (d, J = 7.9 Hz, 1H), 8.35 (d, J = 7.8 Hz, 1H), 10.87 (s, 1H), 12.25-12.95 (br, 1H) |

TABLE 10

| Compound No. | Melting Point (° C.) | $^1$H-NMR Spectrum (δ, DMSO-$d_6$) |
|---|---|---|
| Compound 77 | 209-210 | 1.20 (d, J = 7.0 Hz, 6H) 2.89 (dd, J = 6.8, 13.7 Hz, 1H), 3.08 (dd, J = 8.7, 13.7 Hz, 1H), 3.21-3.25 (m, 1H), 4.60-4.65 (m, 1H), 6.69 (d, J = 15.8 Hz, 1H), 6.96-6.99 (m, 1H), 7.04-7.07 (m, 1H), 7.15 (s, 1H), 7.28 (d, J = 7.9 Hz, 2H), 7.32-7.38 (m, 2H), 7.46 (d, J = 7.9 Hz, 2H), 7.55 (d, J = 7.9 Hz, 1H), 8.34 (d, J = 7.9 Hz, 1H), 10.84 (s, 1H), 12.69 (s, 1H) |
| Compound 78 | — | 1.76-1.77 (m, 3H), 3.02 (dd, J = 9.1, 14.6 Hz, 1H), 3.19 (dd, J = 4.8, 14.6 Hz, 1H), 4.52-4.56 (m, 1H), 5.98 (dd, J = 1.3, 15.4 Hz, 1H), 6.58 (dd, J = 7.1, 15.2 Hz, 1H), 6.96-6.99 (m, 1H), 7.04-7.07 (m, 1H), 7.12 (d, J = 1.6 Hz, 1H), 7.33 (d, J = 8.0 Hz, 1H), 7.53 (d, J = 7.9 Hz, 1H), 8.16 (d, J = 7.9 Hz, 1H), 10.82 (s, 1H), 12.61 (s, 1H) |
| Compound 79 | — | 1.76 (s, 3H), 2.02 (s, 3H), 2.99 (dd, J = 9.1, 14.6 Hz, 1H), 3.17 (dd, J = 4.9, 14.6 Hz, 1H), 4.47-4.51 (m, 1H), 5.71 (d, J = 0.9 Hz, 1H), 6.96-6.99 (m, 1H), 7.04-7.07 (m, 1H), 7.13 (d, J = 1.9 Hz, 1H), 7.33 (d, J = 8.1 Hz, 1H), 7.53 (d, J = 7.9 Hz, 1H), 7.98 (d, J = 7.9 Hz, 1H), 10.81 (s, 1H), 12.54 (s, 1H) |
| Compound 80 | — | 1.66-1.68 (m, 6H), 3.12 (dd, J = 9.4, 14.5 Hz, 1H), 3.22 (dd, J = 4.6, 14.5 Hz, 1H), 4.47-4.51 (m, 1H), 6.28-6.30 (m, 1H), 6.96-6.99 (m, 1H), 7.04-7.07 (m, 1H), 7.15 (s, 1H), 7.33 (d, J = 8.1 Hz, 1H), 7.54 (d, J = 7.9 Hz, 1H), 7.76 (d, J = 7.8 Hz, 1H), 10.81 (s, 1H), 12.58 (s, 1H) |
| Compound 81 | — | 0.87 (t, J = 7.2 Hz, 3H), 1.38-1.42 (m, 2H), 2.08-2.09 (m, 2H), 3.02 (dd, J = 9.3, 14.4 Hz, 1H), 3.18-3.21 (m, 1H), 4.53-4.55 (m, 1H), 5.97 (d, J = 15.5 Hz, 1H), 6.55-6.61 (m, 1H), 6.96-6.99 (m, 1H), 7.04-7.07 (m, 1H), 7.12 (s, 1H), 7.33 (d, J = 8.0 Hz, 1H), 7.53 (d, J = 7.8 Hz, 1H), 8.18 (d, J = 7.7 Hz, 1H), 10.82 (s, 1H), 12.62 (s, 1H) |
| Compound 82 | 95-96 | 1.95 (s, 3H), 3.15-3.20 (m, 1H), 3.26-3.29 (m, 1H), 4.55-4.57 (m, 1H), 6.98-7.00 (m, 1H), 7.06-7.08 (m, 1H), 7.15 (s, 1H), 7.21 (s, 1H), 7.32-7.43 (m, 6H), 7.60 (d, J = 7.8 Hz, 1H), 8.13 (d, J = 7.7 Hz, 1H), 10.86 (s, 1H), 12.69 (s, 1H) |

Example 176

Analgesic Efficacy Test (1)

A compound of the present invention was orally administered to mice, to carry out an analgesic efficacy test according to acetic acid writhing test (nociceptive pain model animal). As an experimental animal, 4-week old male ddY-type mice were previously bred, and thereafter 8 mice per one group were used in the experiment. A solution or suspension prepared by dissolving or suspending a compound of the present invention in a 0.5% (w/v) aqueous CMC-Na solution was orally administered as a test substance in a single dose. While, to a control group, a 0.5% (w/v) aqueous CMC-Na solution was administered in the same manner. After 25 minutes from administration, the mice were intraperitoneally administered with a 0.7% (v/v) acetic acid/physiological saline at the dose of 10 mL/kg. From 5 minutes thereafter, writhing number in a 10-minute period was counted, and a suppressive rate for each individual (mean±standard error) was calculated by the following formula:

$$\text{Suppressive Rate (\%)} = \frac{\text{(Mean Writhing Number of Control Group} - \text{Writhing Number of Each Individual)}}{\text{Mean Writhing Number of Control Group}} \times 100$$

In the test for significance difference, Baltlett's test was carried out in the comparison between multiple groups of the group administered with test substance with the control group. In the case of homoscedasticity, Dunnett's multiple comparison test of parametrics, and in the case of heteroscedasticity, Dunnett's multiple comparison test of non-parametrics were used. In addition, in the test of dose dependency, Jockheere-Terpstra's test was used. In all cases, significance difference was considered to be found at P<0.05.

One example of the above test results is shown in Tables 11 and 12. As a result of conducting the analgesic efficacy test according to acetic acid writhing test, the compounds of the present invention exhibited excellent analgesic effects.

TABLE 11

| Test Substance | Dose of Test Substance (mg/kg) | Percent Suppression (%) |
|---|---|---|
| Compound 1 | 10 | 25.7 ± 6.3* |
| Compound 2 | 10 | 41.8 ± 4.1* |
| Compound 3 | 3 | 36.9 ± 10.6* |
| Compound 4 | 100 | 42.4 ± 8.3 |
| Compound 5 | 10 | 51.3 ± 10.9* |
| Compound 6 | 100 | 39.2 ± 15.4 |
| Compound 7 | 100 | 37.3 ± 11.8 |
| Compound 8 | 10 | 67.7 ± 10.3* |
| Compound 9 | 10 | 41.0 ± 12.9* |
| Compound 10 | 10 | 41.6 ± 9.6* |
| Compound 11 | 100 | 60.9 ± 5.9* |
| Compound 12 | 100 | 34.9 ± 11.5 |
| Compound 13 | 10 | 52.9 ± 7.7* |
| Compound 14 | 10 | 43.2 ± 10.9* |
| Compound 15 | 100 | 61.3 ± 9.9* |
| Compound 16 | 100 | 69.0 ± 4.9* |
| Compound 17 | 10 | 54.7 ± 6.8* |
| Compound 18 | 10 | 56.5 ± 4.2* |
| Compound 19 | 100 | 52.2 ± 6.1* |
| Compound 20 | 100 | 41.6 ± 6.0* |
| Compound 21 | 10 | 38.3 ± 6.5* |
| Compound 22 | 10 | 39.9 ± 8.6* |
| Compound 23 | 100 | 48.2 ± 11.5* |
| Compound 24 | 10 | 35.8 ± 9.3* |
| Compound 25 | 10 | 41.2 ± 11.1* |
| Compound 26 | 10 | 30.5 ± 9.2* |
| Compound 27 | 3 | 45.0 ± 10.0* |
| Compound 28 | 10 | 56.5 ± 5.3* |
| Compound 29 | 10 | 56.8 ± 6.8* |

*P < 0.05 (Dunnett's multiple comparison test)

TABLE 12

| Test Substance | Dose of Test Substance (mg/kg) | Percent Suppression (%) |
|---|---|---|
| Compound 30 | 10 | 35.8 ± 9.9* |
| Compound 31 | 100 | 31.5 ± 9.7 |
| Compound 34 | 10 | 45.2 ± 6.3* |
| Compound 35 | 100 | 55.2 ± 7.4* |
| Compound 36 | 10 | 49.7 ± 11.3* |
| Compound 37 | 10 | 37.9 ± 7.5* |
| Compound 38 | 100 | 52.0 ± 8.2* |
| Compound 40 | 10 | 42.3 ± 7.0* |
| Compound 41 | 100 | 47.3 ± 15.7 |
| Compound 42 | 100 | 52.7 ± 8.3* |
| Compound 43 | 10 | 45.3 ± 10.8* |
| Compound 44 | 10 | 48.0 ± 10.3* |
| Compound 46 | 100 | 38.7 ± 11.3 |
| Compound 47 | 100 | 36.2 ± 11.2* |
| Compound 48 | 10 | 43.2 ± 7.3* |
| Compound 49 | 100 | 31.8 ± 7.0 |
| Compound 50 | 100 | 35.1 ± 15.4 |
| Compound 51 | 10 | 42.2 ± 9.1* |
| Compound 52 | 3 | 50.9 ± 7.4* |
| Compound 53 | 100 | 32.0 ± 14.6 |
| Compound 54 | 100 | 33.3 ± 10.0 |
| Compound 56 | 100 | 48.7 ± 10.1* |
| Compound 61 | 100 | 40.5 ± 7.8* |
| Compound 62 | 10 | 39.2 ± 13.5* |
| Compound 63 | 10 | 41.1 ± 7.8* |
| Compound 64 | 10 | 50.6 ± 7.5* |
| Compound 65 | 100 | 31.6 ± 13.1 |
| Compound 66 | 100 | 56.0 ± 6.9* |
| Compound 67 | 10 | 43.5 ± 6.9* |
| Compound 68 | 100 | 55.4 ± 9.9* |

*P < 0.05 (Dunnett's multiple comparison test)

Example 177

Analgesic Efficacy Test (2)

An analgesic efficacy test was conducted using a Chung model rat, a neuropathic pain model. Using Wistar male rats after passing 9-week old as an experimental animal, a model rat was prepared in accordance with the method of Kim and Chung (Pain, 50, 355-363, 1992). Specifically, left L5 spinal nerves of rats were exposed under anesthetization with pentobarbital (35 mg/kg, intraperitoneal administration), and firmly ligated with 5-0 silk yarn at L5 dorsal root ganglion peripheral side. The animals were placed in a transparent acrylic cage of which bottom was wire netted The measurement of allodynia was carried out using von Frey filament (manufactured by North Coast Medical Inc.) and a 50% reaction threshold was calculated according to an up-down method, in accordance with methods of Chaplan et al. (J. Neurosci. Method, 53, 55-63, 1994) and Lee et al. (J. Neurophysiol., 81, 2226-2233, 1999). The 50% reaction thresholds were measured twice before injury of the spinal nerve, and those animals of which thresholds were outside the standard were removed from the operation of spinal nerve injury. On or after 14 days from the spinal nerve injury, a 50% reaction threshold was measured, and those showing thresholds of 1 g or more and less than 4 g were used as experimental animal. The group was constituted by 7 rats per group so that an average of a 50% reaction threshold for each group would be nearly even.

A solution or suspension prepared by dissolving or suspending a compound of the present invention in a 0.5% (w/v) aqueous CMC-Na solution was orally administered as a test substance in a single dose while, a 0.5% (w/v) aqueous CMC-Na solution was administered in the same manner to the control group for nerve injury. After 30 minutes from the administration, the measurement of allodynia was carried out, and a 50% reaction threshold (mean±standard error) was calculated. In the test for significance difference, Baltlett's test was carried out in the comparison between multiple groups of the group administered with test substance with the control group for nerve injury. In the case of homoscedasticity, Dunnett's multiple comparison test of parametrics, and in the case of heteroscedasticity, Dunnett's multiple comparison test of non-parametrics were used. In all cases, significance difference was considered to be found at P<0.05.

One example of the above test results is shown in Tables 13 and 14. As a result of conducting the analgesic efficacy test using Chung model rats, a neuropathic pain model, the compounds of the present invention exhibited significantly excellent analgesic effects.

TABLE 13

| | | 50% Reaction Threshold (g) | | | |
| | | Control Group for Nerve Injury | | Group Administered with Test Substance | |
| Test Substance | Dose of Test Substance (mg/kg) | Before Administration | 30 Min. After Administration | Before Administration | 30 Min. After Administration |
| --- | --- | --- | --- | --- | --- |
| Compound 1  | 10 | 2.74 ± 0.06 | 2.80 ± 0.16 | 2.74 ± 0.23 | 11.18 ± 1.74* |
| Compound 38 | 1  |             |             | 2.69 ± 0.24 | 5.44 ± 0.75*  |
| Compound 2  | 10 | 2.42 ± 0.19 | 3.10 ± 0.42 | 2.45 ± 0.18 | 11.64 ± 1.81* |
| Compound 39 | 10 |             |             | 2.45 ± 0.23 | 11.44 ± 1.70* |
| Compound 4  | 10 | 2.69 ± 0.12 | 3.83 ± 0.16 | 2.71 ± 0.22 | 10.73 ± 1.59* |
| Compound 5  | 10 |             |             | 2.73 ± 0.20 | 6.87 ± 1.28*  |
| Compound 8  | 10 |             |             | 2.66 ± 0.25 | 8.39 ± 1.30*  |
| Compound 9  | 1  | 2.70 ± 0.20 | 3.54 ± 0.35 | 2.69 ± 0.24 | 6.28 ± 0.42*  |
| Compound 10 | 10 |             |             | 2.73 ± 0.21 | 6.73 ± 1.26   |
| Compound 11 | 10 |             |             | 2.75 ± 0.23 | 10.55 ± 1.50* |
| Compound 13 | 10 | 2.72 ± 0.09 | 3.04 ± 0.44 | 2.74 ± 0.06 | 9.94 ± 1.56*  |
| Compound 14 | 10 |             |             | 2.74 ± 0.06 | 9.38 ± 1.68*  |
| Compound 15 | 10 |             |             | 2.74 ± 0.17 | 9.12 ± 1.55*  |
| Compound 16 | 10 | 2.69 ± 0.12 | 2.49 ± 0.42 | 2.74 ± 0.06 | 8.38 ± 1.07*  |
| Compound 17 | 10 |             |             | 2.74 ± 0.06 | 12.99 ± 1.53* |
| Compound 18 | 10 |             |             | 2.81 ± 0.00 | 11.73 ± 1.60* |
| Compound 19 | 1  | 2.69 ± 0.12 | 2.85 ± 0.17 | 2.67 ± 0.14 | 5.16 ± 0.41*  |
| Compound 20 | 1  |             |             | 2.69 ± 0.12 | 6.13 ± 0.75*  |
| Compound 21 | 1  |             |             | 2.72 ± 0.09 | 3.93 ± 0.16*  |
| Compound 22 | 10 | 2.67 ± 0.14 | 3.02 ± 0.23 | 2.63 ± 0.18 | 11.34 ± 1.52* |
| Compound 64 | 1  |             |             | 2.71 ± 0.22 | 6.21 ± 1.04*  |
| Compound 23 | 10 | 2.62 ± 0.23 | 2.81 ± 0.25 | 2.61 ± 0.24 | 9.37 ± 1.56*  |
| Compound 29 | 10 |             |             | 2.54 ± 0.19 | 6.45 ± 1.39*  |
| Compound 67 | 1  |             |             | 2.52 ± 0.15 | 4.94 ± 0.61*  |

*P < 0.05 (Dunnett's multiple comparison test)

TABLE 14

| | | 50% Reaction Threshold (g) | | | |
| | | Control Group for Nerve Injury | | Control Group for Nerve Damage | |
| Test Substance | Dose of Test Substance (mg/kg) | Before Administration | 30 Min. After Administration | Before Administration | 30 Min. After Administration |
| --- | --- | --- | --- | --- | --- |
| Compound 26 | 1  | 2.69 ± 0.12 | 2.39 ± 0.36 | 2.69 ± 0.12 | 7.71 ± 1.08*  |
| Compound 27 | 1  |             |             | 2.66 ± 0.10 | 7.40 ± 1.17*  |
| Compound 42 | 10 |             |             | 2.69 ± 0.24 | 7.70 ± 1.35*  |
| Compound 28 | 10 | 2.72 ± 0.15 | 2.81 ± 0.30 | 2.69 ± 0.24 | 5.90 ± 1.16*  |
| Compound 36 | 10 |             |             | 2.67 ± 0.25 | 9.01 ± 1.55*  |
| Compound 37 | 1  |             |             | 2.67 ± 0.25 | 8.70 ± 1.26*  |
| Compound 3  | 1  | 2.66 ± 0.10 | 2.52 ± 0.25 | 2.63 ± 0.18 | 6.11 ± 1.54*  |
| Compound 30 | 10 |             |             | 2.63 ± 0.18 | 10.21 ± 1.44* |
| Compound 35 | 1  |             |             | 2.67 ± 0.14 | 6.30 ± 0.19*  |
| Compound 66 | 1  |             |             | 2.63 ± 0.18 | 6.51 ± 1.40*  |
| Compound 34 | 10 | 2.93 ± 0.12 | 2.97 ± 0.21 | 2.93 ± 0.12 | 6.40 ± 0.15*  |
| Compound 43 | 1  |             |             | 2.93 ± 0.12 | 6.68 ± 1.18*  |
| Compound 44 | 1  |             |             | 2.93 ± 0.12 | 5.35 ± 0.53*  |

TABLE 14-continued

| Test Substance | Dose of Test Substance (mg/kg) | 50% Reaction Threshold (g) | | | |
|---|---|---|---|---|---|
| | | Control Group for Nerve Injury | | Control Group for Nerve Damage | |
| | | Before Administration | Before Administration | Before Administration | Before Administration |
| Compound 40 | 1 | 2.61 ± 0.14 | 3.29 ± 0.41 | 2.58 ± 0.15 | 10.28 ± 1.33* |
| Compound 62 | 1 | | | 2.59 ± 0.20 | 9.09 ± 1.63* |
| Compound 47 | 10 | 2.75 ± 0.23 | 2.72 ± 0.37 | 2.69 ± 0.12 | 5.48 ± 0.80* |
| Compound 48 | 10 | | | 2.72 ± 0.09 | 3.02 ± 0.34 |
| Compound 51 | 10 | | | 2.81 ± 0.00 | 7.95 ± 1.08* |
| Compound 52 | 10 | 2.84 ± 0.16 | 2.87 ± 0.28 | 2.79 ± 0.20 | 8.70 ± 1.68* |
| Compound 56 | 10 | | | 2.88 ± 0.07 | 9.32 ± 1.45* |
| Compound 63 | 1 | | | 2.87 ± 0.15 | 6.53 ± 0.72* |
| Compound 59 | 10 | 2.63 ± 0.12 | 3.73 ± 0.51 | 2.65 ± 0.16 | 5.78 ± 1.06 |
| Compound 60 | 10 | | | 2.66 ± 0.18 | 5.43 ± 0.51* |
| Compound 61 | 10 | | | 2.64 ± 0.26 | 9.81 ± 1.60* |

*P < 0.05 (Dunnett's multiple comparison test)

Example 178

Test of Blood Kinetics in the Rats

Ten milligrams of a compound of the present invention was properly converted to a sodium salt with the same amount of sodium hydroxide, where necessary, and each was dissolved in 5 mL of water. Five compounds each among these aqueous solutions of the compounds of the present inventions were mixed, to prepare a mixed solution containing 0.4 mg/mL each of each compound. Six-week old Wistar SPF male rats that were fasted were orally administered with the mixed solution in a single dose using a gavage tube (each compound 2 mg/5 mL/kg, n=5). At time points of 0.25, 0.5, 1, 2, 4, and 8 hours after the administration, about 150 μL of blood was collected using a heparin-added capillary tube from veins of rat tails. The capillary tubes were centrifuged to collect the plasma. The plasma sample was deprotenized and the supernatant was diluted to prepare each of measurement sample solutions. The concentration of the compound of the present invention in each of measurement sample solutions was quantified using LC-MS, and Cmax (maximum concentration in plasma) and AUC (area under the curve for concentration in blood, time 0 to infinite (∞) hours) of the compounds of the present invention were calculated.

One example of the above test results is shown in Table 15. It was confirmed that the compounds of the present invention showed both high values in Cmax and AUC, so that the migration into the blood of rats upon the oral administration is excellent.

TABLE 15

| Test Substance | Cmax (μg/mL) | $AUC_{0-\infty}$ (μg * hr/mL) |
|---|---|---|
| Compound 1 | 7.1 | 24.2 |
| Compound 3 | 5.8 | 26.2 |
| Compound 4 | 4.3 | 28.7 |
| Compound 5 | 2.3 | 14.6 |
| Compound 8 | 5.0 | 21.9 |
| Compound 11 | 1.7 | 10.6 |
| Compound 13 | 7.4 | 46.3 |
| Compound 14 | 4.8 | 33.9 |
| Compound 15 | 2.8 | 19.4 |
| Compound 20 | 3.0 | 10.2 |
| Compound 22 | 4.0 | 11.4 |
| Compound 24 | 15.0 | 148.0 |
| Compound 25 | 1.5 | 6.8 |
| Compound 27 | 53.3 | 403.9 |

TABLE 15-continued

| Test Substance | Cmax (μg/mL) | $AUC_{0-\infty}$ (μg * hr/mL) |
|---|---|---|
| Compound 28 | 37.7 | 182.8 |
| Compound 29 | 50.6 | 237.9 |
| Compound 30 | 3.6 | 13.4 |
| Compound 34 | 3.2 | 16.5 |
| Compound 36 | 2.3 | 11.4 |
| Compound 37 | 1.5 | 6.8 |
| Compound 38 | 2.8 | 8.5 |
| Compound 40 | 48.7 | 61.7 |
| Compound 42 | 18.8 | 57.7 |
| Compound 51 | 33.0 | 115.7 |
| Compound 52 | 18.0 | 38.2 |
| Compound 56 | 3.5 | 7.0 |

INDUSTRIAL APPLICABILITY

As shown in various analgesic efficacy tests described above, the amino acid derivative of the present invention is a compound that shows an excellent analgesic action to not only a model animal for nociceptive pains but also a model animal for neuropathic pains, and also has excellent migration into the blood upon the oral administration. Therefore, the compound of the present invention is very useful as a drug for treating various acute or chronic pain diseases and neuropathic pain diseases such as reflex sympathetic dystrophy, postherpetic neuralgia or diabetic neuropathy for which analgesics such as nonsteroidal anti-inflammatory drugs (NSAIDs) are less likely to effect.

The invention claimed is:

1. An amino acid derivative, and salt and hydrate thereof that is pharmaceutically acceptable, wherein the amino acid derivative is represented by the following general formula (I):

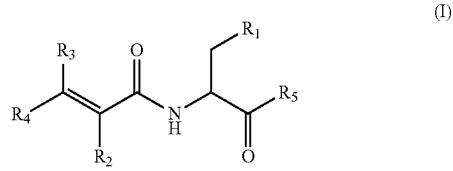

(I)

wherein $R_1$ stands for an indole of which N-position may be substituted with formyl, benzyl, or alkyl having 1 to 6 carbon atoms;

$R_2$ stands for a hydrogen, an alkyl having 1 to 4 carbon atoms, or a cyano;

$R_3$ stands for a hydrogen or an alkyl having 1 to 4 carbon atoms;

$R_4$ stands for a hydrogen, an alkyl having 1 to 4 carbon atoms, or a phenyl which may be substituted with one or two substituents selected from hydroxy, fluorine, cyano, trifluoromethyl, phenoxy, alkyl having 1 to 6 carbon atoms, and alkoxy having 1 to 4 carbon atoms;

$R_5$ stands for a hydroxy or an amino, or $R_2$ and $R_4$ may be bound to form a benzofuran ring or a coumarin ring, with proviso that in a case where $R_2$ is a hydrogen and $R_4$ is a phenyl substituted with one or two hydroxys, where $R_2$ is a hydrogen and $R_4$ is an unsubstituted phenyl, where $R_2$ is a hydrogen and $R_4$ is a phenyl substituted with hydroxy and methoxy, where $R_2$ and $R_4$ are a hydrogen, or where $R_2$ and $R_4$ are bound to form a coumarin ring, $R_1$ stands for an indole of which N-position is substituted with formyl, benzyl, or alkyl having 1 to 6 carbon atoms.

2. The amino acid derivative, or salt or hydrate thereof that is pharmaceutically acceptable according to claim 1, wherein $R_3$ is a hydrogen.

3. The amino acid derivative, or salt or hydrate thereof that is pharmaceutically acceptable according to claim 2, wherein $R_5$ is a hydroxy.

4. The amino acid derivative, or salt or hydrate thereof that is pharmaceutically acceptable according to claim 3, wherein $R_2$ is a hydrogen.

5. The amino acid derivative, or salt or hydrate thereof that is pharmaceutically acceptable according to claim 4, wherein $R_1$ is an indole.

6. The amino acid derivative, or salt or hydrate thereof that is pharmaceutically acceptable according to claim 5, wherein $R_4$ is a phenyl substituted with cyano.

7. The amino acid derivative, or salt or hydrate thereof that is pharmaceutically acceptable according to claim 5, wherein $R_4$ is a phenyl substituted with fluorine.

8. The amino acid derivative, or salt or hydrate thereof that is pharmaceutically acceptable according to claim 5, wherein $R_4$ is a phenyl substituted with hydroxy.

9. The amino acid derivative, or salt or hydrate thereof that is pharmaceutically acceptable according to claim 5, wherein $R_4$ is a phenyl substituted with phenoxy.

10. The amino acid derivative, or salt or hydrate thereof that is pharmaceutically acceptable according to claim 5, wherein $R_4$ is a phenyl substituted with alkoxy having 1 to 4 carbon atoms.

11. The amino acid derivative, or salt or hydrate thereof that is pharmaceutically acceptable according to claim 4, wherein $R_1$ is an indole of which N-position is substituted with alkyl having 1 to 6 carbon atoms.

12. The amino acid derivative, or salt or hydrate thereof that is pharmaceutically acceptable according to claim 11, wherein $R_4$ is a phenyl substituted with cyano.

13. The amino acid derivative, or salt or hydrate thereof that is pharmaceutically acceptable according to claim 11, wherein $R_4$ is a phenyl substituted with fluorine.

14. The amino acid derivative, or salt or hydrate thereof that is pharmaceutically acceptable according to claim 11, wherein $R_4$ is a phenyl substituted with hydroxy.

15. The amino acid derivative, or salt or hydrate thereof that is pharmaceutically acceptable according to claim 11, wherein $R_4$ is a phenyl substituted with phenoxy.

16. The amino acid derivative, or salt or hydrate thereof that is pharmaceutically acceptable according to claim 3, wherein $R_2$ is a cyano.

17. The amino acid derivative, or salt or hydrate thereof that is pharmaceutically acceptable according to claim 3, wherein $R_2$ and $R_4$ are bound to form a benzofuran ring.

18. The amino acid derivative, or salt or hydrate thereof that is pharmaceutically acceptable according to claim 2, wherein $R_5$ is an amino, and $R_2$ is a hydrogen.

19. A pharmaceutical agent comprising:

as an active ingredient an amino acid derivative, or salt or hydrate thereof that is pharmaceutically acceptable; and a pharmaceutically acceptable carrier, wherein the amino acid derivative is represented by the following general formula (I'):

$$\text{(I')}$$

wherein $R_1'$ stands for an indole of which N-position may be substituted with formyl, benzyl, or alkyl having 1 to 6 carbon atoms, a phenyl substituted with hydroxy or alkoxy having 1 to 4 carbon atoms, an alkyl having 1 to 6 carbon atoms which may be substituted with carboxy, amino, guanidino, carbamoyl, or alkylsulfanyl having 1 to 4 carbon atoms, or a hydroxy;

$R_2'$ stands for a hydrogen, an alkyl having 1 to 4 carbon atoms, or a cyano;

$R_3'$ stands for a hydrogen or an alkyl having 1 to 4 carbon atoms;

$R_4'$ stands for a hydrogen, an alkyl having 1 to 4 carbon atoms, or a phenyl which may be substituted with one or two substituents selected from fluorine, cyano, trifluoromethyl, phenoxy, alkyl having 1 to 6 carbon atoms, and alkoxy having 1 to 4 carbon atoms;

$R_5'$ stands for a hydroxy or an amino, or $R_2'$ and $R_4'$ may be bound to form a benzofuran ring or a coumarin ring, with proviso that in a case where $R_2'$ is a hydrogen and $R_4'$ is a phenyl substituted with methyl, $R_1'$ stands for a substituent other than a carboxymethyl.

20. The pharmaceutical agent comprising as an active ingredient an amino acid derivative, or salt or hydrate thereof that is pharmaceutically acceptable according to claim 19, wherein $R_1'$ is an indole.

21. The pharmaceutical agent comprising as an active ingredient an amino acid derivative, or salt or hydrate thereof that is pharmaceutically acceptable according to claim 20, wherein $R_4'$ is a phenyl substituted with cyano or fluorine.

22. The pharmaceutical agent comprising as an active ingredient an amino acid derivative, or salt or hydrate thereof that is pharmaceutically acceptable according to claim 19, wherein $R_1'$ is an indole of which N-position is substituted with alkyl having 1 to 6 carbon atoms.

23. The pharmaceutical agent comprising as an active ingredient an amino acid derivative, or salt or hydrate thereof that is pharmaceutically acceptable according to claim 22, wherein $R_4'$ is a phenyl substituted with cyano or fluorine.

24. An analgesic comprising:

as an active ingredient an amino acid derivative, or salt or hydrate thereof that is pharmaceutically acceptable; and a pharmaceutically acceptable carrier, wherein the amino acid derivative is represented by the following general formula (I"):

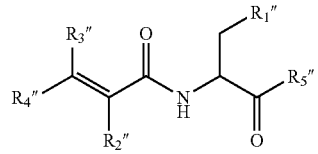

(1")

wherein $R_1''$ stands for an indole of which N-position may be substituted with formyl, benzyl, or alkyl having 1 to 6 carbon atoms, a phenyl substituted with hydroxy or alkoxy having 1 to 4 carbon atoms, an alkyl having 1 to 6 carbon atoms which may be substituted with carboxy, amino, guanidino, carbamoyl, or alkylsulfanyl having 1 to 4 carbon atoms, or a hydroxy;

$R_2''$ stands for a hydrogen, an alkyl having 1 to 4 carbon atoms, or a cyano;

$R_3''$ stands for a hydrogen or an alkyl having 1 to 4 carbon atoms;

$R_4''$ stands for a hydrogen, an alkyl having 1 to 4 carbon atoms, or a phenyl which may be substituted with one or two substituents selected from fluorine, cyano, trifluoromethyl, phenoxy, alkyl having 1 to 6 carbon atoms, and alkoxy having 1 to 4 carbon atoms;

$R_5''$ stands for a hydroxy or an amino, or $R_2''$ and $R_4''$ may be bound to form a benzofuran ring or a coumarin ring, with proviso that in a case where $R_2''$ is a hydrogen and $R_4''$ is a phenyl substituted with methyl, $R_1''$ stands for a substituent other than a carboxymethyl.

25. A method of treating pain comprising administering an effective amount of an amino acid derivative, or salt or hydrate thereof that is pharmaceutically acceptable, to a subject in need thereof, wherein the amino acid derivative is represented by the following general formula (I'):

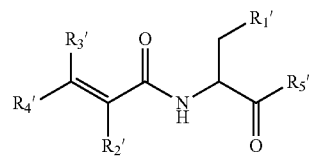

(I')

wherein $R_1'$ stands for an indole of which N-position may be substituted with formyl, benzyl, or alkyl having 1 to 6 carbon atoms, a phenyl substituted with hydroxy or alkoxy having 1 to 4 carbon atoms, an alkyl having 1 to 6 carbon atoms which may be substituted with carboxy, amino, guanidino, carbamoyl, or alkylsulfanyl having 1 to 4 carbon atoms, or a hydroxy;

$R_2'$ stands for a hydrogen, an alkyl having 1 to 4 carbon atoms, or a cyano;

$R_3'$ stands for a hydrogen or an alkyl having 1 to 4 carbon atoms;

$R_4'$ stands for a hydrogen, an alkyl having 1 to 4 carbon atoms, or a phenyl which may be substituted with one or two substituents selected from hydroxy, fluorine, cyano, trifluoromethyl, phenoxy, alkyl having 1 to 6 carbon atoms, and alkoxy having 1 to 4 carbon atoms;

$R_5'$ stands for a hydroxy or an amino, or $R_2'$ and $R_4'$ may be bound to form a benzofuran ring or a coumarin ring, with proviso that in a case where $R_2'$ is a hydrogen and $R_4'$ is a phenyl substituted with methyl, $R_1'$ stands for a substituent other than a carboxymethyl; or in a case where $R_2'$ is a hydrogen and $R_4'$ is a phenyl substituted with one or two hydroxys, $R_1'$ stands for a substituent other than an unsubstituted indole, a hydroxyphenyl, and a carboxymethyl; or in a case where $R_2'$ is a hydrogen and $R_4'$ is a phenyl substituted with hydroxy and alkoxy, $R_1'$ stands for a substituent other than an unsubstituted indole, a guanidinoethyl, and an aminopropyl.

* * * * *